(12) United States Patent
Joshi et al.

(10) Patent No.: US 10,980,751 B2
(45) Date of Patent: Apr. 20, 2021

(54) PHARMACEUTICAL OR NUTRACEUTICAL COMPOSITION WITH RESISTANCE AGAINST THE INFLUENCE OF ETHANOL

(71) Applicant: Evonik Operations GmbH, Essen (DE)

(72) Inventors: Shraddha Joshi, Navi Mumbai (IN); Ashish Guha, Dombivali (IN); Sanjay Lanke, Navi Mumbai (IN); Vinay Jain, Mumbai (IN); Firouz Asgarzadeh, Freehold, NJ (US); Mitulkumar M Patel, East Windsor, NJ (US)

(73) Assignee: Evonik Operations GmbH, Essen (DE)

( * ) Notice: Subject to any disclaimer, the term of this patent is extended or adjusted under 35 U.S.C. 154(b) by 0 days.

(21) Appl. No.: 15/578,746

(22) PCT Filed: May 23, 2016

(86) PCT No.: PCT/EP2016/061551
§ 371 (c)(1),
(2) Date: Dec. 1, 2017

(87) PCT Pub. No.: WO2016/193034
PCT Pub. Date: Dec. 8, 2016

(65) Prior Publication Data
US 2018/0140556 A1  May 24, 2018

(30) Foreign Application Priority Data
Jun. 5, 2015 (IN) .......................... 2843/CHE/2015

(51) Int. Cl.
| | |
|---|---|
| *A61K 9/50* | (2006.01) |
| *A61K 9/16* | (2006.01) |
| *A23L 33/10* | (2016.01) |
| *A61K 31/138* | (2006.01) |
| *A61K 31/167* | (2006.01) |

(52) U.S. Cl.
CPC ............ *A61K 9/5073* (2013.01); *A23L 33/10* (2016.08); *A61K 9/1652* (2013.01); *A61K 9/501* (2013.01); *A61K 9/5026* (2013.01); *A61K 9/5036* (2013.01); *A61K 9/5047* (2013.01); *A61K 9/5089* (2013.01); *A61K 31/138* (2013.01); *A61K 31/167* (2013.01); *A23V 2002/00* (2013.01)

(58) Field of Classification Search
CPC .. A61K 9/5073; A61K 9/1652; A61K 9/5026; A61K 9/5036; A61K 9/5047; A61K 9/5089; A61K 9/501; A61K 31/138; A61K 31/167; A23L 33/10; A23V 2002/00
USPC ........................................................ 424/495
See application file for complete search history.

(56) References Cited

U.S. PATENT DOCUMENTS

| | | | |
|---|---|---|---|
| 6,632,454 B2 | 10/2003 | Beckert et al. | |
| 6,897,205 B2 | 5/2005 | Beckert et al. | |
| 7,438,929 B2 | 10/2008 | Beckert et al. | |
| 8,216,613 B2 | 7/2012 | Gryczke | |
| 2005/0089571 A1 | 4/2005 | Beckert et al. | |
| 2006/0204576 A1 | 9/2006 | Petereit et al. | |
| 2007/0104789 A1 | 5/2007 | Spector | |
| 2008/0050428 A1* | 2/2008 | Ney ................... | A61K 31/4375 424/464 |
| 2008/0107732 A1 | 5/2008 | Dharmadhikari et al. | |
| 2008/0193522 A1 | 8/2008 | Meier et al. | |
| 2008/0206324 A1 | 8/2008 | Gryczke et al. | |
| 2009/0221621 A1* | 9/2009 | Sathyan ............... | A61K 9/0004 514/282 |
| 2010/0151010 A1 | 6/2010 | Petereit et al. | |
| 2010/0247639 A1 | 9/2010 | Ravishankar et al. | |
| 2012/0093926 A1* | 4/2012 | Bodinge .............. | A61K 9/2846 424/463 |

(Continued)

FOREIGN PATENT DOCUMENTS

| | | | | |
|---|---|---|---|---|
| JP | 2012-520831 | | 9/2012 | |
| WO | 2005/101983 A2 | | 11/2005 | |
| WO | WO-2007053698 A2 * | | 5/2007 | ........... A61K 9/2027 |
| WO | 2012/022498 A1 | | 2/2012 | |
| WO | 2014/032741 A1 | | 3/2014 | |
| WO | 2014/032742 A1 | | 3/2014 | |
| WO | WO-2014032741 A1 * | | 3/2014 | ........... A61K 9/2846 |

OTHER PUBLICATIONS

Sonje, A. et al. "Comprehensive Review on Eudragit Polymers" Int. Res. J. Pharm. 2013, 4 (5) (Year: 2013).*

(Continued)

*Primary Examiner* — Andrew S Rosenthal
(74) *Attorney, Agent, or Firm* — Grüneberg and Myers PLLC

(57) ABSTRACT

The invention refers to a pharmaceutical or nutraceutical composition comprising a core a) comprising an active ingredient and a water-insoluble polymer, a coating layer b) above the core a) comprising a salt of an alginic acid, and a coating layer c) above the coating layer b) comprising an anionic (meth)acrylate copolymer polymerized from a (meth)acrylate monomer mixture comprising 5-75% by weight in relation to the total weight of the (meth)acrylate monomer mixture of (meth)acrylate monomers with an anionic group, wherein the amount of the water-insoluble polymer in the core a) is 2 to 20% by weight in relation to the weight of the core a) and the amount of the salt of an alginic acid in the coating layer b) is 5 to 85% by weight in relation to the weight of the core a) and the amount of the anionic (meth)acrylate copolymer in the coating layer c) is 10 to 75% by weight in relation to the weight of the core a) and to the coating layer b).

10 Claims, No Drawings

(56) References Cited

U.S. PATENT DOCUMENTS

2015/0190348 A1 7/2015 Haksar et al.
2015/0209298 A1 7/2015 Haksar et al.

OTHER PUBLICATIONS

Hellmig, S. et al. "Gastric emptying time of fluids and solids in healthy subjects determined by 13C breath tests: influence of age, sex and body" Journal of Gastroenterology and Hepatology 21 (2006) 1832-1838 (Year: 2006).*
Tukaram, B.N. et al. "The Effects of Lactose, Microcrystalline Cellulose and Dicalcium Phosphate on Swelling and Erosion of Compressed HPMC Matrix Tablets: Texture Analyzer" Iranian Journal of Pharmaceutical Research (2010), 9 (4): 349-358 (Year: 2010).*
U.S. Appl. No. 14/416,500, filed Jan. 22, 2015, US 2015-0209298 A1, Priyanka Bansilal Haksar et al.
U.S. Appl. No. 14/416,171, filed Jan. 21, 2015, US 2015-0190348 A1, Priyanka Bansilal Haksar et al.
U.S. Appl. No. 15/518,429, filed Apr. 11, 2017, US 2017-0304211 A1, Shraddha Joshi et al.
U.S. Appl. No. 15/117,062, filed Aug. 5, 2016, US 2016-0354319 A1, Shraddha Sanjeev Joshi et al.
International Search Report and Written Opinion dated Jul. 20, 2016 in PCT/EP2016/061551 filed May 23, 2016.
Mansuri et al., "*Glimpse of Drug Delivery Systems for Proton Pump Inhibitors,*" Int. J. Pharm. Sci. Rev. Res., 36(1), Jan.-Feb. 2016; Article No. 14, pp. 81-88.
Meenakshi Joshi, "*Role of Eudragit in Targeted Drug Delivery,*" Int J Curr Pharm Res, vol. 5, Issue 2, 58-62.

* cited by examiner

PHARMACEUTICAL OR NUTRACEUTICAL COMPOSITION WITH RESISTANCE AGAINST THE INFLUENCE OF ETHANOL

FIELD OF THE INVENTION

The invention is in the field of alcohol resistant pH triggered sustained release formulations.

TECHNICAL BACKGROUND

US 2007/0104789 A1 describes gastro-resistant and ethanol-resistant controlled-release formulations comprising hydromorphone. The gastro-resistant and ethanol-resistant can be used in a matrix as well as the coating of the formulations. Alginic acid is mentioned among the examples for suitable gastro-resistant and—ethanol resistant substances. Pellet cores or granules may be prepared by anhydrous granulation, may be coated with the gastro-resistant and ethanol-resistant substances and then may be filled in capsules or bags or compressed into tablets under addition of dried pharmaceutical or nutraceutically acceptable auxiliary substances.

WO2012/022498A1 describes a gastric resistant pharmaceutical or nutraceutical composition, comprising a core, comprising a pharmaceutical or nutraceutical active ingredient and a gastric resistant coating layer onto the core, wherein the release of the pharmaceutical or nutraceutical active ingredient is not more than 15% under in-vitro conditions at pH 1.2 for 2 hours in a buffered medium according to USP with and without the addition of 40% (v/v) ethanol, wherein the gastric resistant coating layer comprises 50 to 100% by weight of one or more salts of alginic acid with a viscosity of 30 to 720 cP of a 1% aqueous solution (weight/weight) and where the polymer dry weight gain of the coating layer is at least 4 mg/cm2.

WO2014/032742A1 describes a pharmaceutical or nutraceutical composition, comprising a core, comprising a pharmaceutical or a nutraceutical active ingredient and an inner coating layer comprising one or more salts of alginic acid and an outer coating layer comprising one or more water-insoluble polymers or copolymers, wherein the ratio by weight of the amount of the one or more salts of alginic acid in the inner coating layer to the amount of the one or more water-insoluble polymers or copolymers in outer coating layer is at least 2.5:1.

WO2014/032741A1 describes a pharmaceutical or nutraceutical composition, comprising a core, comprising a pharmaceutical or a nutraceutical active ingredient and an inner coating layer comprising at least 30% by weight of one or more salts of alginic acid and an outer coating layer comprising at least 30% by weight of one or more polymers or copolymers comprising anionic side groups.

OBJECT OF THE INVENTION

Pharmaceutical or nutraceutical compositions are designed to release the active ingredient in a manner of reproducible release curves. This shall result in desirable and reliable blood level profiles which shall provide an optimal therapeutic effect. If the blood level concentrations are too low, the active ingredient will not cause a sufficient therapeutic effect. If the blood level concentrations are too high, this may cause toxic effects. In both cases non optimal blood level concentrations of an active ingredient can be dangerous for the patient and shall therefore be avoided. A problem exists in that the ideal ratios assumed for the release of active ingredient during the design of a pharmaceutical or nutraceutical composition can be altered by the general living habits, thoughtlessness or by addictive behaviour of the patients with respect to the use of ethanol or ethanol-containing drinks. In these cases, the pharmaceutical or nutraceutical form which is actually designed for an exclusively aqueous medium is additionally exposed to an ethanol containing medium of greater or lesser strength. Since health authorities like for instance the US Food and Drug Administration (FDA) focus more and more on the ethanol problem, ethanol resistance may be an important registration requirement in the near future.

Since not all patients are aware of the risk of simultaneous taking of a controlled release pharmaceutical or nutraceutical form and ethanol-containing drinks or do not follow or are not able to follow appropriate warnings, advice or recommendations, there is a demand for controlled release pharmaceutical or nutraceutical compositions, especially for gastric resistant pharmaceutical or nutraceutical compositions, such that their mode of action is affected as little as possible by the presence of ethanol.

Conventional gastric resistant pharmaceutical or nutraceutical compositions if coated or uncoated are usually not resistant to alcohol at all. Therefore one problem of the present invention was to provide gastric resistant pharmaceutical or nutraceutical compositions which are resistant against the influence of ethanol.

Especially there is a problem for gastric resistant or enteric formulated compositions. These kinds of formulations are usually coated with a gastric resistant coating layer (enteric coating layer) onto the core which has the function that the release of the pharmaceutical or nutraceutical active ingredient in the stomach, respectively at pH 1.2 for 2 hours according to USP, shall not exceed 10%, preferably less than 5%. This function ensures that acid-sensitive pharmaceutical or nutraceutical active ingredients are protected against inactivation and that pharmaceutical or nutraceutical active ingredients which may be irritate the stomach mucosa are not set free in too high amounts. On the other hand in many cases the release of the pharmaceutical or nutraceutical active ingredient in the intestine, respectively at pH 6.8 for one hour or less according to the USP method, is designed to exceed at least 70, 75% or more. The presence of ethanol in concentrations of 5, 10, 20 or 40% (volume/volume) in the gastric fluid usually leads to an increase to the release rates in the stomach. Due to distribution effect the effect of ingested ethanol is in the intestine not of that importance as in the stomach. Thus an effective protection against the influence of ethanol should prevent such an undesired increase of pharmaceutical or nutraceutical active ingredient in the stomach in the first place. Furthermore it may be desired that protection against the influence of ethanol shall at least not influence the comparably fast release rates at pH 6.8 in media without ethanol.

It was an object of the present invention to provide a pharmaceutical or nutraceutical composition with a gastric resistant release profile which is also resistant against the influence of ethanol at pH 1.2. The gastric resistant release profile should then be followed by a release phase where the active ingredient is released in a sustained manner. Thus the pharmaceutical or nutraceutical composition as disclosed herein is a gastric resistant, ethanol resistant and sustained release pharmaceutical or nutraceutical composition.

DETAILED DESCRIPTION OF THE INVENTION

The invention relates to a pharmaceutical or nutraceutical composition comprising a core a) comprising an active ingredient and a water-insoluble polymer, a coating layer b) above the core a) comprising a salt of an alginic acid, and a coating layer c) above the coating layer b) comprising an anionic (meth)acrylate copolymer polymerized from a (meth)acrylate monomer mixture comprising 5-75% by weight in relation to the total weight of the (meth)acrylate monomer mixture of (meth)acrylate monomers with an anionic group, wherein the amount of the water-insoluble polymer in the core a) is 2 to 50, 2 to 30, 2 to 20% by weight in relation to the weight of the core a) and the amount of the salt of an alginic acid in the coating layer b) is 5 to 85% by weight in relation to the weight of the core a) and the amount of the anionic (meth)acrylate copolymer in the coating layer c) is 10 to 75% by weight in relation to the weight of the core a) and to the coating layer b), wherein, when the amount of polymerized monomers with anionic groups of the anionic (meth)acrylate copolymer comprised in the coating layer c) is 5 to 40% by weight in relation to the total weight of the polymerized monomers, the percentages of the amount of the salt of the alginic acid in the coating layer b) in relation to the weight of the core a) and the percentages of the amount of the anionic (meth)acrylate copolymer in the coating layer c) in relation to the weight of the core a) and the coating layer b) add up to at least 50% or when the amount of polymerized monomers with anionic groups of the anionic (meth)acrylate copolymer comprised in the coating layer c) is more than 40 and up to 75% by weight in relation to the total weight of the polymerized monomers, the percentages of the amount of the salt of the alginic acid in the coating layer b) in relation to the weight of the core a) and the percentages of the amount of the anionic (meth)acrylate copolymer in the coating layer c) in relation to the weight of the core a) and the coating layer b) add up to at least 60%.

The term "polymerized monomers" is understood as the amount of monomers which are used in the polymerzation process.

Gastric Resistant, Ethanol Resistant and Sustained Release Pharmaceutical or Nutraceutical Composition The pharmaceutical or nutraceutical composition as disclosed herein is a gastric resistant, an ethanol resistant and a sustained release pharmaceutical or nutraceutical composition at the same time.

Gastric resistant shall mean that the release of the pharmaceutical or nutraceutical active ingredient is not more than 10%, not more than 8%, not more than 5% under in-vitro conditions at pH 1.2 for 2 hours in medium according to USP (for instance USP32).

Ethanol resistant shall mean that the release of the pharmaceutical or nutraceutical active ingredient is not more than 10%, not more than 8%, not more than 5%, under in-vitro conditions at pH 1.2 for 2 hours in medium according to USP (for instance USP32) with the addition of 40% (v/v) ethanol.

Sustained release shall mean the release of the pharmaceutical or nutraceutical active ingredient is less than 20, 30, 40 or 50% after 4 hours or after 5 hours and at least 60%, at least 70%, at least 80% after 6 to 10 hours or after 8 to 10 hours under in-vitro conditions at pH 1.2 for 2 hours and subsequent buffered medium at pH 6.8 or at pH 7.4 according to USP (for instance USP32) for the remaining time Thus the pharmaceutical or nutraceutical composition shows a release of the pharmaceutical or nutraceutical active ingredient is not more than 10%, not more than 8%, not more than 5%, under in-vitro conditions at pH 1.2 for 2 hours in a medium according to USP (for instance USP32) with and without the addition of 40% (v/v) ethanol.

Thus the pharmaceutical or nutraceutical composition as disclosed is a composition wherein the release of the pharmaceutical or nutraceutical active ingredient is less than 20, less than 30, less than 40, less than 50 or less than 60% after 4 hours or after 5 hours and at least 60, at least 70, at least 80 or at least 90% after 6 to 10 hours or after 8 to 10 hours under in-vitro conditions at pH 1.2 for the first 2 hours and subsequent buffered medium at pH 6.8 or at pH 7.4 (optionally including a follow up of first pH 6.8 and then pH 7.4 buffered medium) according to USP for the remaining time.

The above expression "after 6 to 10 hours or after 8 to 10 hours" refers to the total time from the start of the release test at pH 1.2 and thus includes the first two hours at pH 1.2.

The above expression "buffered medium at pH 6.8 or at pH 7.4" refers to the buffered medium present at the certain time point chosen from the time intervals "after 6 to 10 hours or after 8 to 10 hours". The release test itself may, after the pH 1.2 phase, comprise a pH 6.8 or a pH 7.4 medium phase alone or a follow up of first pH 6.8 and then pH 7.4 medium.

For instance in example F28 the active ingredient release is 74.6% after 8 hours. These 8 hours assemble from 2 hours at pH 1.2 and 6 hours at pH 6.8. After 8 hours the buffered medium is the pH 6.8 medium.

For instance in example F29 the active ingredient release is 73.2% after 8 hours. These 8 hours assemble from 2 hours at pH 1.2, 1 hour at pH 6.8 and 5 hours at pH 7.4. After 8 hours the buffered medium is the pH 7.4 medium.

Core a)

The core a) is comprising, comprising essentially, or consisting of a pharmaceutical or a nutraceutical active ingredient and a water-insoluble polymer.

The core a) may further comprise pharmaceutical or nutraceutically acceptable excipients. The pharmaceutical or a nutraceutical active ingredient, the water-insoluble polymer and the pharmaceutical or nutraceutically acceptable excipients may add up to 100%.

The core a) may be called a sustained release core. A sustained release core may be defined as a core which is formulated in such a way that it releases the included active ingredient upon contact with an aqueous medium, such as a pH 1.2 medium or buffered medium of pH 6.8 or pH 7.4 according to USP (for instance USP32) only slowly, for instance less than 20, 30, 40 or 50% after 4 hours or after 5 hours and at least 60% after 6 to 10 hours or after 8 to 10 hours. The sustained release core a) alone without further coating is not gastric resistant and not ethanol resistant as defined before.

The formulation of the core a) as a sustained release core may be achieved by the formulation of the active ingredient in a matrix of a water-insoluble polymer of the type of or such as EUDRAGIT® NE, EUDRAGIT® NM, EUDRAGIT® RL or EUDRAGIT® RS. In the case of matrix the core a) may preferably comprise 5 to 80, 10 to 50, or 15 to 40% by weight of the water-insoluble polymer.

Alternatively the core a) may comprise an inner core a1), comprising the active ingredient, and a coating layer a2), comprising the water-insoluble polymer, wherein the coating layer a2) is above the inner core a1) and below the coating layer b). In this case the coating layer a2) may preferably comprise 2 to 30, 2 to 20, 10 to 25, 5 to 20% by weight of the water-insoluble polymer in relation to the weight of the total core a) consisting of a1) and a2). The core a1) and/or the coating layer a2) may further comprise pharmaceutical or nutraceutically acceptable excipients to add up to 100%.

Thus the formulation of the core a) as a sustained release core may be achieved alternatively by the formulation of the active ingredient as an immediate release or as an immediate disintegrating core in the form of an inner core a1) and a coating layer a2) which comprises a water-insoluble polymer such as EUDRAGIT® NE, EUDRAGIT® RL or EUDRAGIT® RS.

An immediate release or an immediate disintegrating core a1) is a core which releases the included active ingredient upon contact with an aqueous medium to at least 80 or 100% within 10 minutes.

The core a1) may comprise or may contain a neutral carrier pellet, for instance a sugar sphere or non-pareilles, on top of which the active ingredient may be bound in a binder, such as lactose, celluloses, like micro crystalline cellulose (MCC), or polyvinylpyrrolidon (PVP). In this case the active ingredient may be bound or placed localized at the surface of the core a1) (as a part of the core a)). The binding of the active ingredient at the surface of the core a1) in such a binding layer has usually no effect or influence in the sense of a release control function. In this case the coating layer a2) contributes the sustained release characteristic to the core a) as a whole.

The core a1) may alternatively comprise a pellet in the form of a polymeric matrix in which the active ingredient is bound. The core may comprise an uncoated pellet or granule consisting of a crystallized active ingredient. The core may be as well an active ingredient containing tablet, mini tablet or capsule. In these cases the active ingredient may be placed more or less randomly distributed throughout the core as a whole.

The coating layer a2) may comprise the water-insoluble polymer and optionally a glidant such as talc, silica, or glycerol monostearate (GMS), optionally a plasticizer, such as triethylcitrate (TEC) or a polyethylen gylcol (PEG) and optionally a poreformer (pore-forming agent). Pore forming agents may include celluloses like hydroxypropyl cellulose (HPMC) or hydroxypropyl cellulose (HPC) or natural gums, such as guar gum or xanthan gum, or hydrophilic polymeric materials, such as polyvinyl acetate (PVA). The water-insoluble polymer, the glidant, the plasticizer and/or the poreformer may add up to 100%. The glidant may be about 5 to 200 or 40 to 60% by weight in relation to the water-insoluble polymer, the plasticizer may be about 5 to 25% by weight in relation to the water-insoluble polymer. The poreformer may be about 5 to 200, 40 to 60, 5 to 25, 2 to 80, 2 to 60 or 2 to 40% by weight in relation to the water-insoluble polymer. The water-insoluble polymer, the glidant, the plasticizer or the pore-formimg agent may add up to 100%.

The weight of the coating layer a2) in relation to the weight of the core a1) may be from 2 to 100, 5 to 50 or 10 to 30%.

Coating Layers b) and c)

The pharmaceutical or nutraceutical composition is comprising, comprising essentially or consisting of the core a), the coating layer b) onto or above the core a) and the coating layer c) onto or above the coating layer b).

The coating layers b) and c) have the function of further controlling the release of the active ingredient, which is placed in the core a). The coating layers b) and c) have also the function of providing resistance of the active ingredient release against the presence ethanol.

Preferably the pharmaceutical or nutraceutical composition is comprising, comprising essentially or consisting of the core a), which may comprise an inner core a1) and a coating layer a2), the coating layer b) and the outer coating layer c) and there are no further coating layers present, which would additionally control the release of the active ingredient.

The coating layers b) and c) may interact with the release of the active ingredient from the core a) so that the release rates of the whole system is usually different from that of the core a) alone and could not be predicted before the disclosure of the present application.

The coating layers b) and c) may comprise pharmaceutical or nutraceutically acceptable excipients.

Coating Layer b)

The coating layer b) is located directly or indirectly onto or above the core a) and comprises a salt of an alginic acid.

The amount of the salt of an alginic acid in the coating layer b) may be 5 to 85, 5-75, 10-70, 15-55, 20-50% by weight in relation to the weight of the core a).

A sub coat may be located between the core a) and the coating layer b). A sub coat may have the function to separate substances of the core from substances of the controlling layer which may be incompatible with each other. The sub coat has essentially no influence on the active ingredient release characteristics. Preferably there is no sub coat between the core and the inner coating layer. In this case the inner coating layer is in direct contact with core.

The absolute amount of the salt of an alginic acid the coating layer b) may be in the case of core a) pellets or granules with an average particle size in the range of 50 to 2000, 200 to 1000 μm (average diameter, the determination of the average particle size may be performed by suitable methods known to the skilled person, preferably according to the United States Pharmacopeia 36 (USP) chapter <429> and European Pharmacopeia 7.0 (EP) chapter 2.9.31) to be coated in the range of 2 to 60, preferably 2 to 40 mg/cm2.

The absolute amount of the salt of an alginic acid in the coating layer b) may be in the case of tablets with a size in the range of more than 1 and up to 25 mm (Average diameter or length) in the range of 0.5 to 20, preferably 5 to 20 mg/cm$^2$.

The coating layer b) comprises at least 20, at least 30, at least 40, at least 50, at least 60, at least 70, at least 80, at least 85, at least 90% or up to 100% by weight, 20 to 100, 30 to 90, 40 to 80, 50 to 70% by weight of one or more salts of alginic acid.

The salts of alginic acid may be selected from sodium alginate, potassium alginate, magnesium alginate, lithium alginate or ammonium alginate or mixtures thereof.

The salts of alginic acid used for the inner coating layer may preferably have a viscosity of 30 to 720 cP of a 1% aqueous solution (weight/weight).

The coating layer b) may further comprise pharmaceutical or nutraceutically acceptable excipients. The salts of alginic acid and the pharmaceutical or nutraceutically acceptable excipients may add up to 100%.

The coating layer b) may comprise up to 80, up to 70, up to 60, up to 50, up to 40, up to 30, up to 20, up to 15, up to 10%, 10 to 70, 30 to 60 or 30 to 50% by weight of pharmaceutical or nutraceutically acceptable excipients. The pharmaceutical or nutraceutically acceptable excipients in the inner coating layer b) are different from the salts of alginic acid. The pharmaceutical or nutraceutically acceptable excipients and the salts of alginic acid in the coating layer b) may add up to 100%.

Preferably the coating layer b) comprises less than 10% by weight, less than 5% by weight, less than 1% by weight or any (0%) polymers or copolymers comprising anionic side groups A typical coating b) may for example comprise or contain 40 to 60 or 60 to 80 by weight of one or more salts of alginic acid and 15 to 95 40 to 60 or 20 to 40% by weight of a glidant, for instance talc.

Coating Layer c)

The coating layer c) is located directly or indirectly onto or above the coating layer b).

The coating layer c) above the coating layer b) is comprising an anionic (meth)acrylate copolymer polymerized, preferably radically polymerized, from a (meth)acrylate monomer mixture comprising 5 to 75, 5 to 60, 5 to 40, 5 to 35, 5 to 15, more than 40 and up to 75, 41 to 59, 45-55, 35 to 60 or 40 to 55% by weight, in relation to the total weight of the (meth)acrylate monomer mixture, of an (one or more) anionic (meth)acrylate monomer.

(Meth)acrylate monomers (one or more monomers) with anionic groups are preferably methacrylic acid or acrylic acid.

The monomer mixture may further comprise monomers which are C1-C4 alkyl esters of acrylic or methacrylic acid and which may add up to 100% with the anionic (meth) acrylate monomers.

The (meth)acrylate monomer mixture to be polymerized thus may further comprise 25 to 95, 40 to 95, 60 to 95, 65 to 95, 85 to 95, more than 40 to 65 or 45 to 60, 25 up to less than 60, 41 to 59, 40 to 65, 45-60% by weight of (meth) acrylate monomers which are C1-C4 alkyl esters of acrylic or methacrylic acid. The (meth)acrylate monomer(s) with anionic groups and the monomers which are C1-C4 alkyl esters of acrylic or methacrylic acid may add up to 100%.

(Meth)acrylate monomers which are C1-C4 alkyl esters of acrylic or methacrylic acid are methyl acrylate, ethyl acrylate, propyl acrylate, butyl acrylate, methyl methacrylate, ethyl methacrylate, propyl methacrylate or butyl methacrylate.

Preferred an anionic (meth)acrylate copolymer are polymerized from a monomer mixture is comprising methacrylic acid in combination with methyl acrylate, ethyl acrylate and/or methyl methacrylate.

Unless stated otherwise the term "an anionic (meth) acrylate copolymer" shall be understood in the sense of "one or more anionic (meth)acrylate copolymers" or as "one or more (meth)acrylate copolymers comprising anionic side groups".

The amount of the anionic (meth)acrylate copolymer in the coating layer c) is 10 to 75, 15 to 60, 20 to 50% by weight in relation to the weight of the core a) and the weight coating layer b). To give an example if the weight of the core a) and the weight coating layer b) is together for instance 210 g (100%) and the amount of the anionic (meth)acrylate copolymer in the coating layer c) is 70 g the amount is 33.3%.

A sub coat may be located between the coating layer b) and the coating layer c). The sub coat has essentially no influence on the active ingredient release characteristics. Preferably there is no sub coat between the core and the coating layer b). In this case the coating layer c) is in direct contact with the coating layer b).

A top coat may be located on top of the coating layer c). The top coat may be preferably water-soluble, essentially water-soluble or dispersible. A top coat may have the function of colouring the pharmaceutical or nutraceutical form or protecting from environmental influences for instance from moisture during storage. The top coat may consist out of a binder, for instance a water soluble polymer like a polysaccharide or HPMC, or a sugar compound like saccharose. The top coat may further contain pharmaceutical or nutraceutical excipients like pigments or glidants in high amounts.

The topcoat has essentially no influence on the release characteristics. Preferably there is no top coat onto the coating layer c).

The pharmaceutical or nutraceutical composition may be characterised in that there are except for the optional coating layer a2), the coating layer b) and the coating layer c) no further controlling layers present which control the release the pharmaceutical or a nutraceutical active ingredient.

The coating layer c) is comprising at least 30, at least 40, at least 50, at least 60, at least 70, at least 80, at least 90% or 10 to 80, 40 to 70% by weight of one or more (meth) acrylate copolymers comprising anionic side groups. Preferably the anionic side groups are carboxylic side groups.

The coating layer c) may further comprise pharmaceutical or nutraceutically acceptable excipients. The anionic (meth) acrylate copolymer and the pharmaceutical or nutraceutically acceptable excipients may add up to 100%.

The coating layer c) may comprise up to 70, up to 60, up to 50, up to 40% or 20 to 90, 30 to 60% by weight of pharmaceutical or nutraceutically acceptable excipients. The pharmaceutical or nutraceutically acceptable excipients in the coating layer c) are different from the anionic (meth) acrylate copolymers. Preferably the coating layer c) comprises less than 10% by weight, less than 5% by weight, less than 1% by weight or any (0%) salts of alginic acid.

In a typical coating layer c) the anionic (meth)acrylate copolymer, a plasticizer and a glidant may add up to 100%. In a preferred embodiment the coating layer c) may for example comprise 10-100, 20-90, 40 to 80 or 50 to 70% by weight of the anionic (meth)acrylate copolymer, for instance EUDRAGIT® L100-55 or EUDRAGIT® FS. A plasticizer, such as triethyl citrate (TEC) or polyethylen gylcol, and a glidant, such as talc, glycerol monostearate (GMS) or silica, may be added to give 100%. Preferably 1 to 25, 2 to 15, 4 to 12%, calculated on the anionic (meth)acrylate copolymer, by weight of a plasticizer and 2-200, 40 to 70 or 30 to 55, 30 to 50% of a glidant, calculated on the anionic (meth) acrylate copolymer may be present.

An absolute amount of polymer respectively anionic (meth)acrylate copolymer in the coating layer c) may be in the case of pellets or granules with a size in the range of 50 to 2000 μm (average diameter) in the range of 2 to 60 preferably 2 to 40 mg/cm².

An absolute amount of polymer respectively anionic (meth)acrylate copolymer in the coating layer c) may be in the case of tablets with a size in the range of more than 1 and up to 25 mm (Average diameter or length) in the range of 0.5 to 20, preferably 5 to 20 mg/cm².

Relations of the Core a), the Coating Layer b) and the Coating Layer c)

When the amount of polymerized monomers with anionic groups of the anionic (meth)acrylate copolymer comprised in the coating layer c) is 5 to 40, 20 to 40 preferably 5 to 15 or preferably more than 15 to 40% by weight in relation to the total weight of the polymerized monomers, the percentages of the amount of the salt of the alginic acid in the coating layer b) in relation to the weight of the core a) and the percentages of the amount of the anionic (meth)acrylate copolymer in the coating layer c) in relation to the weight of the core a) and the coating layer b) may add up to at least 50, at least 55%.

To give an example: When the (meth)acrylate copolymer in the coating layer c) is EUDRAGIT® FS or EUDRAGIT® S, the amount of polymerized monomers with anionic groups of the anionic (meth)acrylate copolymer is 10 or 30% respectively by weight in relation to the total weight of the polymerized monomers. In this case, the percentages of the amount of the salt of the alginic acid in the coating layer b) in relation to the weight of the core a) and the percentages of the amount of the anionic (meth)acrylate copolymer in the coating layer c) in relation to the weight of the core a) and the coating layer b) should add up to at least 50 or at least 55%.

When the amount of polymerized monomers with anionic groups of the anionic (meth)acrylate copolymer comprised in the coating layer c) is more than 40 and up to 75, preferably 45 to 55% by weight in relation to the total weight of the polymerized monomers, the percentages of the amount of the salt of the alginic acid in the coating layer b) in relation to the weight of the core a) and the percentages of the amount of the anionic (meth)acrylate copolymer in the coating layer c) in relation to the weight of the core a) and the coating layer b) should preferably add up to at least 60, at least 65%.

To give an example: When the (meth)acrylate copolymer in the coating layer c) is EUDRAGIT® L 30D or EUDRAGIT® L100-55, the amount of polymerized monomers with anionic groups of the anionic (meth)acrylate copolymer is 50% by weight in relation to the total weight of the polymerized monomers. In this case, the percentages of the amount of the salt of the alginic acid in the coating layer b) in relation to the weight of the core a) and the percentages of the amount of the anionic (meth)acrylate copolymer in the coating layer c) in relation to the weight of the core a) and the coating layer b) should preferably add up to at least 60 or at least 65%.

The term "amount of polymerized monomers with anionic groups of the anionic (meth)acrylate copolymer" shall be understood as the amount of anionic monomers initially contained in the monomer mixture which is polymerized to become the anionic (meth)acrylate copolymer. The term "polymerized monomers" is understood as the amount of monomers which are used in the polymerzation process. The terms corresponds to the expected amount of anionic monomers to be contained as polymerized units in the anionic (meth)acrylate copolymer.

Water-Insoluble Polymer

The core a) is comprising a water-insoluble polymer. The term water-insoluble polymer shall be understood in the sense of one or more water-insoluble polymers or one or more water-insoluble copolymers.

Water-insoluble polymers in the sense of the invention are polymers or copolymers which do not dissolve in water or are only swellable in water over of the whole range of pH 1-14. Water-insoluble polymers may be at the same time a polymer or polymers containing not more than 12% of monomer residues with ionic side groups, like for instance EUDRAGIT® NE, EUDRAGIT® NM, EUDRAGIT® RL or EUDRAGIT® RS polymers.

The water-insoluble polymer may be selected from the group of vinyl polymers or vinyl copolymers or from the group of water-insoluble celluloses.

Water-insoluble polymers may be a vinyl copolymer like polyvinylacetate, including derivates of polyvinylacetate. The polyvinylacetate may be present in the form of an aqueous dispersion or an organic solution. One example is the type Kollicoat® SR 30 D, polyvinylacetate dispersion, stabilized with povidone and Na-laurylsulfate.

Suitable water-insoluble polymers may belong to the group of water-insoluble celluloses. A suitable water-insoluble cellulosic polymer is ethyl cellulose (EC).

Preferably the water-insoluble polymer is a water-insoluble (meth)acrylate copolymer.

Such a water-insoluble (meth)acrylate copolymer may be a polymer polymerized from a monomer mixture selected from more than 95 and up to 100% by weight from of $C_1$ to $C_4$ alkyl esters of (meth)acrylic acid and 0 to less than 5% by weight of (meth)acrylate monomers with an anionic group.

Such a water-insoluble (meth)acrylate copolymer may be a polymer polymerized from a monomer mixture selected from 88 to 98% by weight of $C_1$ to $C_4$ alkyl esters of (meth)acrylic acid and 2 to 12% by weight of alkyl(meth) acrylate monomers with a quaternary ammonium group in the alkyl radical.

Other kinds of water-insoluble polymers in the sense of the invention may be vinyl copolymers like polyvinylacetates, including polyvinylacetate and derivates of polyvinylacetate. The polyvinylacetates may be present in the form of a dispersion. One example is the type Kollicoat® SR 30 D (BASF), polyvinylacetate dispersion, stabilized with povidone and Na-laurylsulfate.

EUDRAGIT® NE 30D/EUDRAGIT® NM 30D—Type Polymers

The core a) may comprise a water-insoluble copolymer which is a copolymer composed of polymerized units of more than 95% by weight, in particular to an extent of at least 98% by weight, preferably to an extent of at least 99% by weight, in particular to an extent of at least 99% by weight, more preferably to an extent of 100% by weight, of (meth)acrylate monomers with neutral radicals, especially $C_1$- to $C_4$-alkyl radicals. These kinds of polymers do not dissolve in water or are only swellable in water over of the whole range of pH 1-14.

Suitable (meth)acrylate monomers with neutral radicals are, for example, methyl methacrylate, ethyl methacrylate, butyl methacrylate, methyl acrylate, ethyl acrylate, butyl acrylate. Preference is given to methyl methacrylate, ethyl acrylate and methyl acrylate.

Methacrylate monomers with anionic radicals, for example acrylic acid and/or methacrylic acid, may be present in small amounts of less than 5% by weight, preferably by not more than 2% by weight, more preferably by not more than 1 or by 0.05 to 1 or by 0 to 0.5% by weight.

Suitable examples are neutral or virtually neutral (meth) acrylate copolymers composed of 20 to 40% by weight of ethyl acrylate, 60 to 80% by weight of methyl methacrylate and 0 to less than 5% by weight, preferably 0 to 2 or 0.05 to 1% or by 0 to 0.5% by weight of methacrylic acid or any methacrylic acid (EUDRAGIT® NE 30D or EUDRAGIT® NM 30D type).

EUDRAGIT® NE 30D and Eudragit® NM 30D are dispersions containing 30% by weight of copolymers composed of free-radically polymerized units of 30% by weight of ethyl acrylate and 70% by weight of methyl methacrylate.

Preference is given to neutral or essentially neutral methyl acrylate copolymers which, according to WO 01/68767, have been prepared as dispersions using 1-10% by weight of a nonionic emulsifier having an HLB value of 15.2 to 17.3. The latter offer the advantage that there is no phase separation with formation of crystal structures by the emulsifier (Eudragit® NM 30D type).

According to EP 1 571 164 A2, corresponding, virtually neutral (meth)acrylate copolymers with small proportions of 0.05 to 1% by weight of monoolefinically unsaturated C3-C8-carboxylic acids can, however, also be prepared by emulsion polymerization in the presence of comparatively small amounts of anionic emulsifiers, for example 0.001 to 1% by weight.

EUDRAGIT® RL/RS-Type Polymers

The core a) may comprise a water-insoluble copolymer which is a copolymer composed of free-radical polymerized units from a monomer mixture of 85 to 98% by $C_1$ to $C_4$ alkyl esters of acrylic or methacrylic acid and 15 to 2% by weight of (meth)acrylate monomers with a quaternary ammonium group in the alkyl radical. These kinds of polymers do not dissolve in water or are only swellable in water over of the whole range of pH 1-14.

Preferred C1 to C4 alkyl esters of acrylic or methacrylic acid are methyl acrylate, ethyl acrylate, butyl acrylate, butyl methacrylate and methyl methacrylate.

The particularly preferred (meth)acrylate monomer with quaternary amino groups is 2 trimethylammoniumethyl methacrylate chloride.

An appropriate copolymer may be composed for example of 50 to 75% by weight of methyl methacrylate, 25 to 45% by weight of ethyl acrylate and 7 to 2% by weight of 2 trimethylammoniumethyl methacrylate chloride.

A specifically suitable copolymer comprises 65% by weight of methyl methacrylate, 30% by weight of ethyl acrylate and 5% by weight of 2 trimethylammoniumethyl methacrylate chloride (EUDRAGIT® RS).

A further suitable (meth)acrylate copolymer may be composed for example of 85 to less than 93% by weight of C1 to C4 alkyl esters of acrylic or methacrylic acid and more than 7 and up to to 15% by weight of (meth)acrylate monomers with a quaternary amino group in the alkyl radical. Such (meth)acrylate monomers are commercially available and have long been used for release-slowing coatings.

An appropriate copolymer may be composed for example of 50 to 70% by weight of methyl methacrylate, 25 to 45% by weight of ethyl acrylate and more than 7 and up to 15% by weight of 2 trimethylammoniumethyl methacrylate chloride.

A specifically suitable copolymer comprises for example 60% by weight of methyl methacrylate, 30% by weight of ethyl acrylate and 10% by weight of 2 trimethylammoniumethyl methacrylate chloride (EUDRAGIT® RL).

Anionic (Meth)Acrylate Copolymer

The coating layer c) is comprising a (meth)acrylate copolymer polymerized from a (meth)acrylate monomer mixture with an amount of monomers with anionic groups of 5-75% by weight in relation to the total weight of the monomer mixture thus it is an anionic (meth)acrylate copolymer. The term an anionic (meth)acrylate copolymer shall be understood in the sense of one or more anionic (meth)acrylate copolymers.

The term "monomer mixture" refers to a mixture of (meth)acrylate monomers which gives 100%. The monomer mixture may be polymerized by addition of polymerization initiators and optionally molecular weight regulators to give a a (meth)acrylate copolymer as well known by a skilled person in the art. The individual amounts of (meth)acrylate monomers that are initially present in the mixture to be polymerized are expected to be contained as polymerized units in the resulting (meth)acrylate copolymer. Statistical variations between the initial present amounts of (meth) acrylate monomers in the monomer mixture and the amounts of polymerized units in the resulting (meth)acrylate copolymer are considered as insignificant.

The one or more polymers or copolymers comprising anionic side groups may comprise 25 to 95, preferably 40 to 95, in particular 60 to 40, % by weight free-radical polymerized $C_1$- to $C_{18}$-alkyl esters, preferably to $C_1$- or $C_1$- to $C_4$-alkyl esters alkyl esters of acrylic or of methacrylic acid and 75 to 5, preferably 60 to 5, in particular 40 to 60, % by weight (meth)acrylate monomers having an anionic side group, respectively a carboxylic side group.

The proportions of (meth)acrylate monomers mentioned normally add up to 100% by weight. However it is also possible in addition, without this leading to an impairment or alteration of the essential properties, for small amounts in the region of 0 to 10, for example 1 to 5, % by weight of further monomers capable of vinylic copolymerization, such as hydroxylated (meth)acrylate monomers, for example, hydroxyethyl methacrylate or hydroxyethyl acrylate, to be present. It is however preferred that no further of such monomers capable of vinylic copolymerization are present.

$C_1$- to $C_4$-alkyl esters of acrylic or methacrylic acid are in particular methyl methacrylate, ethyl methacrylate, butyl methacrylate, methyl acrylate, ethyl acrylate and butyl acrylate.

A (meth)acrylate monomer having an anionic group, respectively a carboxylic side group, may be, for example, acrylic acid, with preference for methacrylic acid.

Examples for Suitable Anionic (Meth)Acrylate Copolymers

A suitable anionic (meth)acrylate copolymer may be comprising, essentially comprising, containing or consisting of polymerized units from a monomer mixture of 10 to 40% by weight of acrylic or methacrylic acid 10 to 80% by weight of a $C_4$- to $C_{18}$-alkyl ester of acrylic or methacrylic acid and optionally 0 to 60% by weight of another vinylic monomers without cross-linking side chains.

$C_4$- to $C_{18}$-alkyl ester of acrylic or methacrylic acid are preferably chosen from n-butyl methacrylate, 2-ethylhexyl acrylate, 2-ethylhexyl methacrylate, isodecyl methacrylate and lauryl methacrylate.

Another vinylic monomer is a vinylic monomer which is not acrylic or methacrylic acid or a $C_4$- to $C_{18}$-alkyl ester of acrylic or methacrylic acid. Another vinylic monomer may be preferably a $C_1$- to $C_3$-alkyl ester of acrylic or methacrylic acid, which are methyl acrylate, ethyl acrylate, propyl acrylate, methyl methacrylate, ethyl methacrylate or propyl methacrylate. Another vinylic monomer may be hydroxyethyl methacrylate, hydroxypropyl methacrylate, poly(ethylenglycol)methylether acrylat, poly(ethylenglycol) methylether methacrylat, poly(propylenglycol)methylether acrylat, poly(propylenglycol)methylether methacrylat or styrene.

Preferably the anionic (meth)acrylate copolymer is comprising, essentially comprising or containing polymerized units out of 10 to 40% by weight of acrylic or methacrylic acid 10 to 50% by weight of ethyl acrylate 10 to 80% by weight of a $C_4$- to $C_{18}$-alkyl ester of acrylic or methacrylic acid and optionally 0 to 20 by weight of methyl methacrylate.

Preferably the anionic (meth)acrylate copolymer is comprising, essentially comprising or containing polymerized units out of 20 to 40% by weight of methacrylic acid, 20 to 40% by weight of n-butyl methacrylate and 30 to 50% by weight of ethyl acrylate Preferably the anionic (meth)acrylate copolymer is comprising, essentially comprising or containing polymerized units from a monomer mixture of
20 to 40% by weight of methacrylic acid,
30 to 50% by weight of 2-ethylhexyl acrylate,
15 to 40% by weight of ethyl acrylate and optionally
0 to 20% by weight of methyl methacrylate.

Preferably the anionic (meth)acrylate copolymer is comprising, essentially comprising or containing polymerized units from a monomer mixture of
10 to 40% by weight of methacrylic acid,
20 to 70% by weight of 2-ethylhexyl methacrylate and
10 to 50% by weight of ethyl acrylate.

Preferably the anionic (meth)acrylate copolymer is comprising, essentially comprising or containing polymerized units from a monomer mixture of
20 to 40% by weight of methacrylic acid,
20 to 50% by weight of 2-ethylhexyl methacrylate and
20 to 50% by weight of ethyl acrylate.

Preferably the anionic (meth)acrylate copolymer is comprising, essentially comprising or containing polymerized units from a monomer mixture of
10 to 35% by weight of methacrylic acid,
40 to 70% by weight of 2-ethylhexyl methacrylate and
10 to 30% by weight of ethyl acrylate.

Preferably the anionic (meth)acrylate copolymer is comprising, essentially comprising or containing polymerized units from a monomer mixture of
20 to 40% by weight of methacrylic acid,
20 to 40% by weight of isodecyl methacrylate and
40 to 50% by weight of ethyl acrylate.

Preferably the anionic (meth)acrylate copolymer is comprising, essentially comprising or containing polymerized units from a monomer mixture of
20 to 40% by weight of methacrylic acid,
20 to 40% by weight of lauryl methacrylate and
30 to 50% by weight of ethyl acrylate.

Further Characteristics of the Anionic (Meth)Acrylate Copolymers,

Further characteristics of the anionic (meth)acrylate copolymer, especially of the anionic (meth)acrylate copolymers described above may be summarized as follows.

Preferably the (meth)acrylate copolymer may be characterized by a mean glass transition temperature from 25 to 120 or 40 to 80° C. (determined by DSC according to DIN EN ISO 11357).

Preferably the (meth)acrylate copolymer may be characterized by a minimum film forming temperature of 50° C. or less (determined according to DIN ISO 2115).

Preferably the (meth)acrylate copolymer may be characterized by a mean molecular weight $M_w$ is 80.000 or more (determined by gel permeation chromatography, GPC).

Further Suitable Anionic (Meth)Acrylate Copolymer

Suitable anionic (meth)acrylate copolymers are those composed of or out of 40 to 60% by weight methacrylic acid and 60 to 40% by weight methyl methacrylate or 60 to 40% by weight ethyl acrylate (EUDRAGIT® L100 or EUDRAGIT® L100-55 types).

EUDRAGIT® L 30D-55 (previously named EUDRAGIT® L 30D) is a 30% by weight aqueous dispersion of a copolymer polymerized from 50% by weight ethyl acrylate and 50% by weight methacrylic acid. The pH of the start of the specific active ingredient release in intestinal juice or simulated intestinal fluid can be stated to be pH 6.0.

EUDRAGIT® L 100-55 is a copolymer polymerized from 50% by weight ethyl acrylate and 50% by weight methacrylic acid. EUDRAGIT® L30 D-55 is a dispersion comprising 30% by weight EUDRAGIT® L 100-55. The pH of the start of the specific active ingredient release in intestinal juice or simulated intestinal fluid can be stated to be pH 5.5.

Likewise suitable are anionic (meth)acrylate copolymers polymerized from or composed of or out of 20 to 40% by weight methacrylic acid and 80 to 60% by weight methyl methacrylate (EUDRAGIT® S type). The pH of the start of the specific active ingredient release in intestinal juice or simulated intestinal fluid can be stated to be pH 7.0.

Suitable (meth)acrylate copolymers are those consisting of 10 to 30% by weight methyl methacrylate, 50 to 70% by weight methyl acrylate and 5 to 15% by weight methacrylic acid (EUDRAGIT® FS type). The pH at the start of the specific active ingredient release in intestinal juice or simulated intestinal fluid can be stated to be pH 7.0.

EUDRAGIT® FS is a copolymer polymerized from or composed of or out of 25% by weight methyl methacrylate, 65% by weight methyl acrylate and 10% by weight methacrylic acid. EUDRAGIT® FS 30 D is a dispersion comprising 30% by weight EUDRAGIT® FS.

Additionally a suitable is a copolymer may be composed of
20 to 34% by weight methacrylic acid and/or acrylic acid,
20 to 69% by weight methyl acrylate and
0 to 40% by weight ethyl acrylate and/or where appropriate
0 to 10% by weight further monomers without cross-linking side chains capable of vinylic copolymerization,
with the proviso that the glass transition temperature of the copolymer according to ISO 11357-2, subsection 3.3.3 (midpoint temperature $T_{mg}$), is not more than 60° C. This (meth)acrylate copolymer is particularly suitable, because of its good elongation at break properties, for compressing pellets to tablets.

Additionally a suitable is a copolymer may be composed of or out of
20 to 33% by weight methacrylic acid and/or acrylic acid,
5 to 30% by weight methyl acrylate and
20 to 40% by weight ethyl acrylate and
more than 10 to 30% by weight butyl methacrylate and where appropriate
0 to 10% by weight further monomers without cross-linking side chains capable of vinylic copolymerization, where the proportions of the monomers add up to 100% by weight,
with the proviso that the glass transition temperature of the copolymer according to ISO 11357-2, subsection 3.3.3 (midpoint temperature $T_{mg}$), is 55 to 70° C. Copolymers of this type are particularly suitable, because of its good mechanical properties, for compressing pellets to tablets.

The above mentioned copolymer is composed in particular of free-radical polymerized units of 20 to 33, preferably 25 to 32, particularly preferably 28 to 31% by weight methacrylic acid or acrylic acid, with preference for methacrylic acid,
5 to 30, preferably 10 to 28, particularly preferably 15 to 25% by weight methyl acrylate,
20 to 40, preferably 25 to 35, particularly preferably 18 to 22% by weight ethyl acrylate, and more than 10 to 30, preferably 15 to 25, particularly preferably 18 to 22% by weight butyl methacrylate,
where the monomer composition is chosen so that the glass transition temperature of the copolymer is from 55 to 70° C., preferably 59 to 66, particularly preferably 60 to 65° C.

Glass transition temperature means in this connection in particular the midpoint temperature $T_{mg}$ according to ISO 11357-2, subsection 3.3.3. Measurement takes place without added plasticizer, with residual monomer contents (REMO) of less than 100 ppm, with a heating rate of 10° C./min and under a nitrogen atmosphere.

The copolymer preferably consists essentially to exclusively of 90, 95 or 99 to 100% by weight of the monomers methacrylic acid, methyl acrylate, ethyl acrylate and butyl methacrylate in the ranges of amounts indicated above.

However, it is possible, without this necessarily leading to an impairment of the essential properties, for small amounts in the range from 0 to 10, e.g. 1 to 5% by weight of further monomers capable of vinylic copolymerization additionally to be present, such as, for example, methyl methacrylate, butyl acrylate, hydroxyethyl methacrylate, vinyl pyrrolidone, vinylmalonic acid, styrene, vinyl alcohol, vinyl acetate and/or derivatives thereof.

Preparation of Anionic (Meth)Acrylate Copolymers

The anionic (meth)acrylate copolymers may be prepared in a manner known per se by free-radical polymerization of the monomers (see, for example, EP 0 704 207 A2 and EP 0 704 208 A2) by radical polymerisation of the monomers in the presence of polymerisation initiators and optionally molecular weight regulators. The copolymers according to the invention may be prepared by free-radical emulsion polymerization in aqueous phase in the presence of, preferably, anionic emulsifiers. The process of emulsion polymerization is well known in the art for instance as described in DE-C 2 135 073.

The average molecular weight Mw (weight average, determined for example by measuring the solution viscosity) of the anionic (meth)acrylate copolymers may be for example in the range from 80 000 to 1 000 000 (g/mol).

Process for Preparing an Anionic (Meth)Acrylate Copolymer

An anionic (meth)acrylate copolymer may be produced by radical polymerisation of the monomers in the presence of polymerisation initiators. Molecular weight regulators may be added. The preferred polymerisation method is emulsion polymerisation.

Properties of the Pharmaceutical or Nutraceutical Composition

The pharmaceutical or nutraceutical composition may be characterized in that the release of the pharmaceutical or nutraceutical active ingredient is not more than 10%, preferably is not more than 5% under in-vitro conditions at pH 1.2 for 2 hours in a buffered medium according to USP with and without the addition of 40% (v/v) ethanol.

The pharmaceutical or nutraceutical composition may be characterized in that the release of the pharmaceutical or nutraceutical active ingredient is less than 60% after 4 hours and at least 60% after 6 to 10 hours under in-vitro conditions at pH 1.2 for 2 hours and subsequent buffered medium at pH 6.8 or at pH 7.4 according to USP for the remaining time.

Salts of Alginic Acid

The salts of alginic acid may be selected from sodium alginate, potassium alginate, magnesium alginate, lithium alginate or ammonium alginate or any kind mixtures thereof.

Viscosity

The salts of alginic acid may have a viscosity of 30 to 720, preferably 40 to 450, preferably 40 to 400 or preferably 50 to 300 centipoise (cP) of a 1% aqueous solution (weight/weight); ([1 cP=1 mPas [mPas]).

The methodology of determination of the viscosity of a polymer solution, for instance a solution of a salt of alginic acid, is well known to the skilled person. The viscosity is preferably determined according to European Pharmacopeia $7^{th}$ edition, general chapter 2, methods of analysis, 2.2.8 and 2.2.10, page 27ff. The test is performed using a spindle viscometer.

The viscosity of a 1% alginate solution may be determined by adding 3 g product to 250 ml of distilled water in a beaker while stirring at 800 rpm using overhead stirrer. Then additional 47 ml water were added with rinsing the walls of the beaker. After stirring for 2 hours and getting a complete solution, the viscosity is measured using a LV model of the Brookfield viscometer at 25° C. (77° F.) at 60 rpm with no. 2 spindle for samples with a viscosity of more than 100 cP and at 60 rpm with no. 1 spindle for samples with viscosity less than 100 cP. Since the weight of water is almost exactly 1 g/ml even at 25° C. "weight/weight" is regarded as equal or identical to "weight/volume" in the sense of the invention. Theoretically possible marginal differences are regarded as insignificant.

Pharmaceutical or Nutraceutical Active Ingredient

The core a) or the inner core a1) may comprise up to 80, up to 60, up to 50, up to 30%, 5 to 95, 10 to 70, 25 to 60, 30 to 55, 30 to 50, 10-30, 5-20% by weight of an active ingredient (pharmaceutical or nutraceutical active ingredient).

Nutraceuticals

The invention is preferably useful for nutraceutical dosage forms.

Nutraceuticals can be defined as extracts of foods claimed to have medical effects on human health. The nutraceutical is usual contained in a medical format such as capsule, tablet or powder in a prescribed dose. Examples for nutraceuticals are resveratrol from grape products as an antioxidant, soluble dietary fiber products, such as psyllium seed husk for reducing hypercholesterolemia, broccoli (sulphane) as a cancer preservative, and soy or clover (isoflavonoids) to improve arterial health. Other nutraceuticals examples are flvonoids, antioxidants, alpha-linoleic acid from flax seed, beta-carotene from marigold petals or antocyanins from berries. Sometimes the expression neutraceuticals is used as synonym for nutraceuticals.

The gastric resistant pharmaceutical or nutraceutical composition is comprising a core, comprising a pharmaceutical or nutraceutical active ingredient. The pharmaceutical or nutraceutical active ingredient may be a pharmaceutical or nutraceutical active ingredient which may be inactivated under the influence of gastric fluids at pH 1.2 or a pharmaceutical or nutraceutical active ingredient which may irritate the stomach mucosa when set free in the stomach.

Pharmaceutical Active Ingredients

The invention is also preferably useful for enteric coated pharmaceutical dosage forms.

Therapeutical and chemical classes of drugs used in enteric coated pharmaceutical dosage forms are for instance analgetics, antibiotics or anti-infectives, antibodies, antiepileptics, antigens from plants, antirheumatics, betablocker, benzimidazole derivatives, beta-blocker, cardiovascular drugs, chemotherapeuitcs, CNS drugs, digitalis glycosides, gastrointestinal drugs, e.g. proton pum inhibitors, enzymes, hormons, liquid or solid natural extracts, oligonucleotides, peptidhormon proteins, therapeutical bacteria, peptides, proteins, proton pump inhibitors, (metal)salt f.e. aspartates, chlorides, orthates, urology drugs, vaccines Examples of drugs, which are acid-lablile, irritating or need controlled release, may be: Acamprosat, aescin, amylase, acetylsalicylic acid, adrenalin, 5-amino salicylic acid, aureomycin, bacitracin, balsalazine, beta carotene, bicalutamid bisacodyl, bromelain, bromelain, budesonide, calcitonin, carbamacipine, carboplatin, cephalosporins, cetrorelix, clarithromycin, chloromycetin, cimetidine, cisapride, cladribine, clorazepate, cromalyn, 1-deaminocysteine-8-D-arginine-vasopressin, deramciclane, detirelix, dexlansoprazole, diclofenac, didanosine, digitoxin and other digitalis glycosides, dihydrostreptomycin, dimethicone, divalproex, drospirenone, duloxetine, enzymes, erythromycin, esomeprazole, estrogens, etoposide, famotidine, fluorides, garlic oil, glucagon, granulocyte colony stimulating factor (G-CSF), heparin, hydrocortisone, human growth hormon (hGH), ibuprofen, ilaprazole, insulin, Interferon, Interleukin, Intron A, ketoprofen, lansoprazole, leuprolidacetat lipase, lipoic acid, lithium, kinin, memantine, mesalazine, metoprolol, metoprolol succinate, methenamine, milameline, minerals, minoprazole, naproxen, natamycin, nitrofurantion, novobiocin, olsalazine, omeprazole, orothates, pancreatin, pantoprazole, paracetamol, parathyroidhormone, paroxetine, penicillin, perprazol, pindolol, polymyxin, potassium, pravastatin, prednisone, preglumetacin progabide, pro-somatostatin, protease, quinapril, rabeprazole, ranitidine, ranolazine, reboxetine, rutosid, somatostatin streptomycin, subtilin, sulfasalazine, sulphanilamide, tamsulosin, tenatoprazole, theophylline, thrypsine, valproic acid, vasopressin, vitamins, zinc, including their salts, derivatives, polymorphs, isomorphs, or any kinds of mixtures or combinations thereof.

Pharmaceutical or Nutraceutical Composition

The pharmaceutical or nutraceutical composition as disclosed herein may be a coated tablet, a coated minitablet, a coated pellet, a coated granule, a sachet, a capsule, filled with coated pellets or with powder or with granules, or a coated capsule, filled with coated pellets or with powder or with granules.

The term coated tablet includes pellet-containing tablets or compressed tablets and is well known to a skilled person. Such a tablet may have a size of around 5 to 25 mm for instance. Usually, defined pluralities of small active ingredient containing pellets are compressed therein together with binding excipients to give the well known tablet form. After oral ingestion and contact with the body fluid the tablet form is disrupted and the pellets are set free. The compressed tablet combines the advantage of the single dose form for ingestion with the advantages of a multiple forms, for instance the dosage accuracy.

The term coated minitablet is well known to the skilled person. A minitablet is smaller than the traditional tablet and may have a size of around 1 to 4 mm. The minitablet is, like a pellet, a single dosage form to be used in multiple dosages. In comparison to pellets, which may be in the same size, minitablets usually have the advantage of having more regular surfaces which can be coated more accurately and more uniformly. Minitablets may be provided enclosed in capsules, such as gelatine capsules. Such capsules disrupt after oral ingestion and contact with the gastric or intestinal fluids and the minitablets are set free. Another application of minitablets is the individual fine adjustment of the active ingredient dosage. In this case the patient may ingest a defined number of minitablets directly which matches to the severe of the decease to cure but also to his individual body weight. A minitablet is different from pellet-containing compressed tablet as discussed above.

The term sachet is well known to the skilled person. It refers to small sealed package which contains the active ingredient often in pellet containing liquid form or also in dry pellet or powder form. The sachet itself is only the package form is not intended to be ingested. The content of the sachet may be dissolved in water or as an advantageous feature may be soaked or ingested directly without further liquid. The latter is advantageous feature for the patient when the dosage form shall be ingested in a situation where no water is available. The sachet is an alternative dosage form to tablets, minitablets or capsules.

Coated pellets may be filled in a capsule, for instance gelatine or HPMC capsule. A capsule containing pellets may also be coated with the enteric coating layer according to the invention.

The gastric resistant pharmaceutical or nutraceutical composition is preferably present in the form of an aqueous coating solution, suspension or dispersion. The dry weight content of the solution, suspension or dispersion may be in the range of 10 to 50, preferably 15 to 35%.

Pharmaceutical or Nutraceutically Acceptable Excipients

The Pharmaceutical or nutraceutical composition may comprise pharmaceutical or nutraceutically acceptable excipients selected from the group of antioxidants, brighteners, binding agents, flavouring agents, flow aids, fragrances, glidants, penetration-promoting agents, pigments, plasticizers, polymers, different from salts of alginic acid and different from the water-insoluble polymers or cellulosic polymers, pore-forming agents or stabilizers or combinations thereof. The pharmaceutical or nutraceutically acceptable excipients may be comprised in the core and/or in the inner coating layer and/or in the outer coating layer.

The core a), the coating layer b) and/or coating layer c) may comprise pharmaceutical or nutraceutically acceptable excipients which may add up to 100% with each of the essential components, e.g. the pharmaceutical or nutraceutical active ingredient, the water-insoluble polymer, the salt of an alginic acid or the anionic (meth)acrylate copolymer.

The core a), the coating layer b) and/or coating layer c) may comprise up to 90, up to 80, up to 70, up to 60, up to 50, up to 40, up to 30% by weight of pharmaceutical or nutraceutically acceptable excipients.

Pharmaceutical or nutraceutically acceptable excipients may be selected from the group of antioxidants, brighteners, binding agents, flavouring agents, flow aids, fragrances, glidants, penetration-promoting agents, polymers (different from the salts of alginic acid and different from the polymers or copolymers comprising anionic side groups; excipient polymers can be for instance disintegrants like crosslinked polyvinyl pyrrolidone), pigments, plasticizers, pore-forming agents or stabilizers or combinations thereof.

Process for Preparing a Pharmaceutical or Nutraceutical Form

A suitable process for preparing the pharmaceutical or nutraceutical composition as disclosed in here may be by forming the core comprising the active ingredient by direct compression, compression of dry, wet or sintered granules, by extrusion and subsequent rounding off, by wet or dry granulation, by direct pelleting or by binding powders onto active ingredient-free beads or neutral cores or active ingredient-containing particles and by applying the inner coating layer and the outer coating layer in the form of aqueous dispersions or organic solutions in spray processes or by fluidized bed spray granulation.

Top Coat and Sub Coats

The pharmaceutical or nutraceutical composition as disclosed herein may be further coated with a sub coat or a top coat or both.

A sub coat may be located between the core and the inner coating layer. A sub coat may have the function to separate substances of the core from substances of the controlling layer which may be incompatible with each other. The sub coat has essentially no influence on the active ingredient release characteristics. A subcoat is preferably essentially water-soluble, for instance it may consist of substances like hydroxypropylmethyl-cellulose (HPMC) as a film former. The average thickness of the subcoat layer is very thin, for example not more than 15 µm, preferably not more than 10 µm.

A top coat may be located on top of the outer coating layer. A top coat is also preferably essentially water soluble. A top coat may have the function of colouring the pharmaceutical or nutraceutical form or protecting from environmental influences for instance from moisture during storage. The top coat may consist out of a binder, for instance a water soluble polymer like a polysaccharide or HPMC, or a sugar compound like saccharose. The top coat may further contain pharmaceutical or nutraceutical excipients like pigments or glidants in high amounts. The topcoat has essentially no influence on the release characteristics.

The expressions sub coat and top coat are well known to the person skilled in the art.

Pellet/Granule/Tablet/Minitablet/Sachet/Capsule

Pharmaceutical or nutraceutical composition may be a coated tablet, a coated minitablet, a coated pellet, a coated granule, a sachet, a capsule, filled with coated pellets or with powder or with granules, or a coated capsule.

Pellets or granules may be used as cores or in compressed tablets. As a rough estimation pellets may have a size in the range of 50 to 2000 µm (average diameter), while coated tablets may have a size in the range of above 2000 µm up to 25 mm (diameter or or length). As a rule one can say the smaller the size of the pellet cores are, the higher the pellet coating weight gain needed. This is due to the comparably higher surface area of pellets compared to tablets.

The term pellet-containing tablet or compressed tablet is well known to a skilled person. Such a tablet may have a size of around 5 to 25 mm for instance. Usually, defined pluralities of small active ingredient containing pellets are compressed therein together with binding excipients to give the well known tablet form. After oral ingestion and contact with the body fluid the tablet form is disrupted and the pellets are set free. The compressed tablet combines the advantage of the single dose form for ingestion with the advantages of a multiple forms, for instance the dosage accuracy. In tablets coatings comparably low amounts of excipients, preferably talcum but also other excipients, may be used in contrast to pellets.

The term minitablet is well known to the skilled person. A minitablet is smaller than the traditional tablet and may have a size of around 1 to 4 mm. The minitablet is, like a pellet, a single dosage form to be used in multiple dosages. In comparison to pellets, which may be in the same size, minitablets usually have the advantage of having more regular surfaces which can be coated more accurately and more uniformly. Minitablets may be provided enclosed in capsules, such as gelatine capsules. Such capsules disrupt after oral ingestion and contact with the gastric or intestinal fluids and the minitablets are set free. Another application of minitablets is the individual fine adjustment of the active ingredient dosage. In this case the patient may ingest a defined number of minitablets directly which matches to the severe of the decease to cure but also to his individual body weight. A minitablet is different from pellet-containing compressed tablet as discussed above.

The term sachet is well known to the skilled person. It refers to small sealed package which contains the active ingredient often in pellet containing liquid form or also in dry pellet or powder form. The sachet itself is only the package form is not intended to be ingested. The content of the sachet may be dissolved in water or as an advantageous feature may be soaked or ingested directly without further liquid. The latter is advantageous feature for the patient when the dosage form shall be ingested in a situation where no water is available. The sachet is an alternative dosage form to tablets, minitablets or capsules.

The term capsule is well known to the skilled person. A capsule is like the sachet a container for pellets containing liquids or also dry pellets or powders. However in contrast to the sachet the capsule consists of pharmaceutically acceptable excipients such as gelatine or hydroxypropylmethylcellulose and is intended to be ingested like a tablet. The capsules disrupts after oral ingestion and contact with the gastric or intestinal fluids and the contained multiple units are set free. Capsules for pharmaceutical purposes are commercially available in different standardized sizes.

Use

The pharmaceutical or nutraceutical composition as described herein may be used as a sustained release gastric resistant pharmaceutical or nutraceutical composition with resistance against the influence of ethanol.

Items

The application is concerned with the following items:

Item 1: A pharmaceutical or nutraceutical composition comprising a core a) comprising an active ingredient and a water-insoluble polymer, a coating layer b) above the core a) comprising a salt of an alginic acid, and a coating layer c) above the coating layer b) comprising an anionic (meth)acrylate copolymer polymerized from a (meth)acrylate monomer mixture comprising 5-75% by weight, in relation to the total weight of the (meth)acrylate monomer mixture, of (meth)acrylate monomers with an anionic group, wherein the amount of the water-insoluble polymer in the core a) is 2 to 50% by weight in relation to the weight of the core a) and the amount of the salt of an alginic acid in the coating layer b) is 5 to 85% by weight in relation to the weight of the core a) and the amount of the anionic (meth)acrylate copolymer in the coating layer c) is 10 to 75% by weight in relation to the weight of the core a) and the weight of the coating layer b), wherein, when the amount of polymerized monomers with anionic groups of the anionic (meth)acrylate copolymer comprised in the coating layer c) is 5 to 40% by weight in relation to the total weight of the polymerized monomers, the percentages of the amount of the salt of the alginic acid in the coating layer b) in relation to the weight of the core a) and the percentages of the amount of the anionic (meth)acrylate copolymer in the coating layer c) in relation to the weight of the core a) and the coating layer b) add up to at least 50% or when the amount of polymerized monomers with anionic groups of the anionic (meth)acrylate copolymer comprised in the coating layer c) is more than 40 and up to 75% by weight in relation to the total weight of the polymerized monomers, the percentages of the amount of the salt of the alginic acid in the coating layer b) in relation to the weight of the core a) and the percentages of the amount of the anionic (meth)acrylate copolymer in the coating layer c) in relation to the weight of the core a) and the coating layer b) add up to at least 60%.

Item 2: Pharmaceutical or nutraceutical composition, according to item 1, wherein the core a) comprises an inner core a1), comprising the active ingredient and a coating layer a2), comprising the water-insoluble polymer, wherein the coating layer a2) is above the inner core a1) and below the coating layer b).

Item 3: Pharmaceutical or nutraceutical composition according to items 1 or 2, wherein the water-insoluble polymer is selected from the group of vinyl polymers or vinyl copolymers or from the group of water-insoluble celluloses.

Item 4: Pharmaceutical or nutraceutical composition, according to any of items 1 to 3, wherein the water-insoluble polymer is a (meth)acrylate copolymer.

Item 5: Pharmaceutical or nutraceutical composition, according to item 4, wherein the water-insoluble polymer is a (meth)acrylate copolymer polymerized from a monomer mixture comprising 88 to 98% by weight of $C_1$ to $C_4$ alkyl esters of (meth)acrylic acid and 2 to 12% by weight of alkyl(meth)acrylate monomers with a quaternary ammonium group in the alkyl radical.

Item 6: Pharmaceutical or nutraceutical composition, according to item 4, wherein the water-insoluble polymer is a (meth)acrylate copolymer which is polymerized from a monomer mixture comprising more than 95 and up to 100% by weight of $C_1$ to $C_4$ alkyl esters of (meth)acrylic acid and 0 to less than 5% by weight of (meth)acrylate monomers with an anionic group.

Item 7: Pharmaceutical or nutraceutical composition, according to any of items 1 to 6, wherein the salt of the alginic acid used for the coating layer b) has a viscosity of 30 to 720 cP in a 1% aqueous solution (weight/weight).

Item 8: Pharmaceutical or nutraceutical composition according to any of items 1 to 7, wherein the salt of alginic acid is selected from sodium alginate, potassium alginate, magnesium alginate, lithium alginate or ammonium alginate or any mixtures thereof.

Item 9: Pharmaceutical or nutraceutical composition, according to any of items 1 to 8, wherein the release of the pharmaceutical or nutraceutical active ingredient is not more than 10% under in-vitro conditions at pH 1.2 for 2 hours in a medium according to USP with and without the addition of 40% (v/v) ethanol.

Item 10: Pharmaceutical or nutraceutical composition according to any of items 1 to 9, wherein the release of the pharmaceutical or nutraceutical active ingredient is less than 60% after 4 hours and at least 60% after 6 to 10 hours under in-vitro conditions at pH 1.2 for 2 hours and subsequent buffered medium at pH 6.8 or at pH 7.4 according to USP for the remaining time.

Item 11: Pharmaceutical or nutraceutical composition according to any of items 1 to 10, wherein the core a), the coating layer b) and/or the coating layer c) comprise up to 80% by weight of pharmaceutical or nutraceutically acceptable excipients.

Item 12: Process for producing the pharmaceutical or nutraceutical composition according to one or more items 1 to 11 by forming the core comprising the active ingredient by direct compression, compression of dry, wet or sintered granules, by extrusion and subsequent rounding off, by wet or dry granulation, direct pelleting or by binding powders onto active ingredient-free beads or neutral cores or active ingredient-containing particles and by applying the inner coating layer and the outer coating layer in the form of aqueous dispersions or organic solutions in spray processes or by fluidized bed spray granulation.

Item 13: Use of a pharmaceutical or nutraceutical composition according to one or more items 1 to 11 as a sustained release gastric resistant pharmaceutical or nutraceutical composition with resistance against the influence of ethanol.

EXAMPLES

Analytical Methodology
Dissolution Media Preparation
Preparation of 0.1N HCl, pH 6.8 Buffer & pH 7.4 Buffer: As Per USP.
Preparation of 40% Alcoholic HCl (Alcoholic Media):
Accurately measured 400 ml of Ethanol was added to 600 ml of 0.1N HCl and mixed.
Dissolution Parameters for Pellets Coated with EUDRAGIT®L30D55

| Parameters | Acid Stage | Buffer Stage |
|---|---|---|
| Apparatus | USP-II (Paddle) | USP-II (Paddle) |
| Volume | 900 mL | 500 mL |
| Dissolution Media | 0.1N HCl/40% Alcoholic HCl | pH 6.8 buffer |
| Temperature | 37.0° C. ± 0.5° C. | 37.0° C. ± 0.5° C. |
| RPM | 50 | 50 |
| Time points | 2 hrs. | 3, 4, 5, 6, 8, 10 & 12 hrs. |

Dissolution Parameters for Pellets Coated with EUDRAGIT®FS30D

| Parameters | Acid Stage | Buffer Stage 1 | Buffer Stage 2 |
|---|---|---|---|
| Apparatus | USP-II (Paddle) | USP-II (Paddle) | USP-II (Paddle) |
| Volume | 900 mL | 500 mL | 500 mL |
| Dissolution Media | 0.1N HCl/40% ethanolic HCl | pH 6.8 buffer | pH 7.4 buffer |
| Temperature | 37.0° C. ± 0.5° C. | 37.0° C. ± 0.5° C. | 37.0° C. ± 0.5° C. |
| RPM | 50 | 50 | 50 |
| Time points | 2 hrs. | 3 hrs. | 4, 5, 6, 7, 8, 9, 10 & 12 hrs. |

Metoprolol Succinate
Assay Method:
The assay of Metoprolol succinate pellets was detected chromatographically.
Chromatographic Condition, Preparation of Buffer & Standard Solution:
As per USP
Preparation of Sample Solution:
Weighed accurately and transferred powder equivalent to 100 mg of Metoprolol Succinate into 100 ml volumetric flask. Added 5 ml of Water and 30 ml of Ethanol and sonicated for 60 min. with shaking in-between, then to that added 25 mL of 0.1N HCl and again sonicated for 30 min. allowed it to cool at room temperature and volume was made up to the mark with 0.1N HCl. 3 ml of this solution was diluted to 50.0 ml with mobile phase. This sample solution was filtered through 0.45p Nylon filter.
Procedure:
Separately injected equal volumes of Blank, standard and sample preparations.
Dissolution Method:
The dissolution of Metoprolol succinate pellets was detected chromatographically.
For Pellets Coated with EUDRAGIT®L30D55
Dissolution Parameters and Media Preparation:

Same as mentioned earlier.
Chromatographic Condition:
As per USP
Preparation of Standard Stock Solution:
Weighed accurately about 47.5 mg of Metoprolol succinate working standard and transferred into a 50 ml volumetric flask. Added about 25 ml of Methanol and sonicated to dissolve then volume was made up to the mark with water.
Preparation of Acid Stage Standard Solution:
5 mL of standard stock solution was diluted to 25 ml with 0.1N HCl or 40% Alcoholic HCl.
Preparation of Buffer Stage Standard Solution (pH 6.8 Buffer):
10 mL of standard stock solution was diluted to 25 ml with pH 6.8 buffer.
Preparation of Sample Solution:
Weighed and transferred each 190 mg equivalent of Metoprolol succinate pellets in six dissolution jars and performed the dissolution test as per parameters given in the method above. This sample solution was filtered through 0.45 μm nylon membrane syringe filter discarded first 2 mL of the filtrate. Filtrate was used as sample.
Procedure:
The dissolution apparatus was set as per parameters. Transferred 190 mg equivalent of Metoprolol succinate and carried out the dissolution.
For Pellets Coated with EUDRAGIT®FS30D
Dissolution Parameters and Media Preparation:
Same as mentioned earlier.
Chromatographic Condition:
As per USP
Preparation of Standard Stock Solution:
Weighed accurately about 47.5 mg of Metoprolol succinate working standard and transferred into a 50 ml volumetric flask. Added about 25 ml of
Methanol and Sonicated to Dissolve then Volume was Made Up to the Mark with Water.
Preparation of Acid Stage Standard Solution:
5 mL of standard stock solution was diluted to 25 ml with 0.1N HCl or 40% Alcoholic HCl.
Preparation of Buffer Stage 1 Standard Solution (pH 6.8 Buffer):
10 mL of standard stock solution was diluted to 25 ml with pH 6.8 buffer.
Preparation of Buffer Stage 2 Standard Solution (pH 7.4 Buffer):
10 mL of standard stock solution was diluted to 25 ml with pH 7.4 buffer.
Preparation of Sample Solution:
Weighed and transferred each 190 mg equivalent of Metoprolol succinate pellets in six dissolution jars and performed the dissolution test as per parameters given in the method above. This sample solution was filtered through 0.45 μm nylon membrane syringe filter discarded first 2 mL of the filtrate. Filtrate was used as sample.
Procedure:
The dissolution apparatus was set as per parameters. Transferred 190 mg equivalent of Metoprolol succinate and carried out the dissolution.
Acetaminophen Assay Method: The assay of Acetaminophen was detected chromatographically.
Chromatographic Condition
Column: Agilent Zorbax C18 column, 150×4.6 mm, 5 μm or equivalent
Column Temp: 25° C.
Injection volume: 20 μL
Wavelength: 295 nm
Run time: 6.0 minutes
Retention time: About 2.3 min.
Flow: 1.0 mL/min
Mobile Phase Preparation:
Mixture of Water:Methanol:Solution A in a ratio 70:30:1 was prepared.
Preparation of Solution A:
A mixture of ortho phosphoric acid and water in the ratio 1:9 was prepared.
Preparation of Standard Solution:
Weighed accurately about 30.0 mg of Acetaminophen working standard and transferred into a 50 ml volumetric flask. Added about 25 ml of water and sonicated to dissolve then volume was made up to the mark with water. 10 ml of this solution was diluted to 25 ml with the mobile phase.
Preparation of Sample Solution:
Weighed accurately and transferred pellets equivalent to 120 mg of Acetaminophen into 200 ml volumetric flask. Added 100 ml of diluent and sonicated for 60 minutes. Allowed it to cool at room temperature and volume was made up to the mark with diluent. 10 ml of this solution was diluted to 25 ml with mobile phase. This sample solution was filtered through 0.45p Nylon filter.
Diluent:
A mixture of water and methanol in the ratio 70:30 was prepared.
Procedure:
Separately injected equal volumes of Blank, standard and sample preparations.
Dissolution Method:
The dissolution of Acetaminophen pellets was detected chromatographically
For pellets coated with EUDRAGIT®L30D55
Dissolution Parameters and Media Preparation:
Same as mentioned earlier.
Chromatographic Condition:
Chromatographic conditions were same as that mentioned in the Assay.
Preparation of Standard Stock Solution:
Weighed accurately about 30.0 mg of Acetaminophen working standard and transferred into a 50 ml volumetric flask. Added about 25 ml of water and sonicated to dissolve then volume was made up to the mark with water.
Preparation of Standard for Acid Stage:
5 ml of stock solution was diluted to 25 ml with dissolution media
Preparation of Standard for buffer stage:
10 ml of stock solution was diluted to 25 ml with dissolution media
Preparation of Sample Solution:
Accurately weighed pellets equivalent to 120 mg of Acetaminophen was transferred in six dissolution jars and performed the dissolution test as per parameters given in the method above. This sample solution was filtered through 0.45 μm nylon membrane syringe filter discarded first 2 mL of the filtrate. Filtrate was used as sample.
Procedure:
The dissolution apparatus was set as per parameters. Pellets equivalent to 120 mg of Acetaminophen was added in each dissolution vessel and the dissolution test was carried out.
For Pellets Coated with EUDRAGIT®FS30D
Dissolution Parameters and Media Preparation:
Same as mentioned earlier.
Chromatographic Condition:
Chromatographic conditions were same as that mentioned in the Assay.

Preparation of Standard Stock Solution:

Weighed accurately about 30.0 mg of Acetaminophen working standard and transferred into a 50 ml volumetric flask. Added about 25 ml of water and sonicated to dissolve then volume was made up to the mark with water.

Preparation of Standard for Acid Stage:

5 ml of stock solution was diluted to 25 ml with dissolution media

Preparation of Standard Solution for Buffer Stage 1 (pH 6.8 Buffer):

10 mL of standard stock solution was diluted to 25 ml with pH 6.8 buffer.

Preparation of Standard Solution for Buffer Stage 2 (pH 7.4 Buffer):

10 mL of standard stock solution was diluted to 25 ml with pH 7.4 buffer.

Preparation of Sample Solution:

Accurately weighed pellets equivalent to 120 mg of Acetaminophen was transferred in six dissolution jars and performed the dissolution test as per parameters given in the method above. This sample solution was filtered through 0.45 μm nylon membrane syringe filter discarded first 2 mL of the filtrate. Filtrate was used as sample.

Procedure:

The dissolution apparatus was set as per parameters. Pellets equivalent to 120 mg of Acetaminophen was added in each dissolution vessel and the dissolution test was carried out.

Formulation Details
List of Ingredients

TABLE 1

| S. No. | Name of excipient | Manufacturer/Supplier | Specification |
|---|---|---|---|
| 1. | Metoprolol succinate | Polydrugs, India | USP |
| 2. | Acetaminophen | Bharat Chemicals | USP |
| 3. | MCC (Avicel ® PH 101) | FMC | USP/NF |
| 4. | Vivapur ® MCG 611P | JRS | USP/NF |
| 5. | EUDRAGIT ® RS 30D | Evonik Industries AG, Germany | NF |
| 6. | EUDRAGIT ® NE30D | Evonik Industries AG, Germany | NF/Ph.Eur |
| 7. | EUDRAGIT ® L 30D-55 | Evonik Industries AG, Germany | NF/Ph.Eur |
| 8. | EUDRAGIT ® S100 | Evonik Industries AG, Germany | NF/Ph.Eur |
| 9. | EUDRAGIT ® FS 30D | Evonik Industries AG, Germany | . . . |
| 10. | Sodium alginate (Protanal ™ CR) | BASF | NF/Ph.Eur |
| 11. | Talc | Luzenac | USP |
| 12. | Triethyl Citrate | Jungbunzlauer | USP/Ph.Eur |
| 13. | Ethyl cellulose | N. Shrikant & Co. | — |
| 14. | Di-butyl sebacate | Vertellus | NF |
| 15. | Hydroxypropyl cellulose-LM | Nippon Soda. Co. Ltd | — |

Unless stated otherwise the figures in the formulation tables refer to grams.

TABLE 2

Examples F1-F12

| Ingredients/ main polymer components (% SA + % FS) | F1/C1 7.5% RS + 10% SA + 20% FS (30%) | F2/C2 15% RS + 20% FS | F3/C3 15% RS + 10% SA + 20% FS (30%) | F4/C4 15% RS + 20% SA + 20% FS (40%) | F5 15% RS + 30% SA + 20% FS (50%) | F6 15% RS + 60% SA + 20% FS (80%) | F7 7.5% RS + 10% SA + 40% FS (50%) | F8/C8 15% RS + 40% FS | F9 15% RS + 10% SA + 40% FS -0.5 | F10 15% RS + 20% SA + 40% FS -0.6 | F11 15% RS + 30% SA + 40% FS -0.7 | F12 15% RS + 60% SA + 40% FS -1 |
|---|---|---|---|---|---|---|---|---|---|---|---|---|
| Inner core a1 of the Core a) | | | | | | | | | | | | |
| Metoprolol succinate | 50 | 50 | 50 | 50 | 50 | 50 | 50 | 50 | 50 | 50 | 50 | 50 |
| MCC(Avicel ® PH 101) | 20 | 20 | 20 | 20 | 20 | 20 | 20 | 20 | 20 | 20 | 20 | 20 |
| Vivapur MCG 611 | 30 | 30 | 30 | 30 | 30 | 30 | 30 | 30 | 30 | 30 | 30 | 30 |
| Water | qs | qs | qs | qs | qs | qs | qs | qs | Qs | qs | qs | qs |
| | 100.00 | 100.00 | 100.00 | 100.00 | 100.00 | 100.00 | 100.00 | 100.00 | 100.00 | 100.00 | 100.00 | 100.00 |
| Coating layer a2) of the Core a) | | | | | | | | | | | | |
| EUDRAGIT ®RS 30D | 7.50* | 15.00* | 15.00* | 15.00* | 15.00* | 15.00* | 7.50* | 15.00* | 15.00* | 15.00* | 15.00* | 15.00* |
| TEC | 1.13 | 2.25 | 2.25 | 2.25 | 2.25 | 2.25 | 1.13 | 2.25 | 2.25 | 2.25 | 2.25 | 2.25 |
| Talc | 3.75 | 7.50 | 7.50 | 7.50 | 7.50 | 7.50 | 3.75 | 7.50 | 7.50 | 7.50 | 7.50 | 7.50 |
| Water | qs | qs | qs | qs | qs | qs | qs | qs | qs | qs | qs | qs |
| | 112.38 | 124.75 | 124.75 | 124.75 | 124.75 | 124.75 | 112.38 | 124.75 | 124.75 | 124.75 | 124.75 | 124.75 |
| Coating layer b) | | | | | | | | | | | | |
| Sodium alginate (Protanal CR) | 11.24 | . . . | 12.48 | 24.95 | 37.43 | 74.85 | 11.24 | . . . | 12.48 | 24.95 | 37.43 | 74.85 |
| Talc | 5.62 | . . . | 6.24 | 12.48 | 18.72 | 37.43 | 5.62 | . . . | 6.24 | 12.48 | 18.72 | 37.43 |
| Water | qs | . . . | qs | qs | qs | qs | qs | . . . | Qs | qs | qs | qs |
| | 129.24 | | 143.75 | 162.18 | 180.90 | 237.03 | 129.24 | | 143.75 | 162.18 | 180.90 | 237.03 |

TABLE 2-continued

Examples F1-F12

| Ingredients/ main polymer components (% SA + % FS) | F1/C1 7.5% RS + 10% SA + 20% FS (30%) | F2/C2 15% RS + 20% FS | F3/C3 15% RS + 10% SA + 20% FS (30%) | F4/C4 15% RS + 20% SA + 20% FS (40%) | F5 15% RS + 30% SA + 20% FS (50%) | F6 15% RS + 60% SA + 20% FS (80%) | F7 7.5% RS + 10% SA + 40% FS (50%) | F8/C8 15% RS + 40% FS | F9 15% RS + 10% SA + 40% FS -0.5 | F10 15% RS + 20% SA + 40% FS -0.6 | F11 15% RS + 30% SA + 40% FS -0.7 | F12 15% RS + 60% SA + 40% FS -1 |
|---|---|---|---|---|---|---|---|---|---|---|---|---|
| *Coating layer c)* | | | | | | | | | | | | |
| EUDRAGIT ® FS 30D | 25.85* | 24.95* | 28.75* | 32.44* | 36.18* | 47.41* | 51.70* | 49.9* | 57.50* | 64.87* | 72.36* | 94.81* |
| TEC | 1.29 | 1.25 | 1.44 | 1.62 | 1.81 | 2.37 | 2.56 | 2.50 | 2.88 | 3.24 | 3.62 | 4.74 |
| Talc | 12.93 | 12.48 | 14.38 | 16.22 | 18.09 | 23.71 | 25.85 | 24.95 | 28.75 | 32.44 | 36.18 | 47.41 |
| Water | qs | qs | qs | qs | qs | qs | qs | qs | qs | qs | qs | qs |
| Total | 169.31 | 163.43 | 188.32 | 212.46 | 236.98 | 310.52 | 209.35 | 202.10 | 232.88 | 262.73 | 293.06 | 383.99 |

*Dry polymer;
F/C = Comparative Examples;
F = Inventive Examples;
SA = Sodium Alginate;
RS = EUDRAGIT ® RS;
FS = EUDRAGIT ® FS (dry) out of EUDRAGIT ® FS 30D;
otherwise weight in grams is indicated

TABLE 3

Examples F13-F21

| Ingredients/main polymer components (% SA + % L) | F13/C13 7.5% RS + 30% SA + 20% L (50%) | F14/C14 15% RS, 20% L | F15/C15 15% RS + 30% SA + 20% L (50%) | F16 15% RS + 60% SA + 20% L (80%) | F17 15% RS + 80% SA + 20% L (100%) | F18 7.5% RS + 30% SA + 40% L (70%) | F19/C19 15% RS + 40% L | F20 15% RS + 30% SA + 40% L (70%) | F21 15% RS + 60% SA + 40% L (100%) |
|---|---|---|---|---|---|---|---|---|---|
| *Inner core a1) of the Core a)* | | | | | | | | | |
| Metoprolol succinate | 50 | 50 | 50 | 50 | 50 | 50 | 50 | 50 | 50 |
| MCC (Avicel PH 101) | 20 | 20 | 20 | 20 | 20 | 20 | 20 | 20 | 20 |
| MCC CL 611 | 30 | 30 | 30 | 30 | 30 | 30 | 30 | 30 | 30 |
| Water | qs | qs | qs | qs | qs | qs | qs | qs | qs |
|  | 100.00 | 100.00 | 100.00 | 100.00 | 100.00 | 100.00 | 100.00 | 100.00 | 100.00 |
| *Coating layer a2) of the Core a)* | | | | | | | | | |
| EUDRAGIT ® RS 30 D | 7.50* | 15.00* | 15.00* | 15.00* | 15.00* | 7.50* | 15.00* | 15.00* | 15.00* |
| TEC | 1.13 | 2.25 | 2.25 | 2.25 | 2.25 | 1.13 | 2.25 | 2.25 | 2.25 |
| Talc | 3.75 | 7.50 | 7.50 | 7.50 | 7.50 | 3.75 | 7.50 | 7.50 | 7.50 |
| Water | qs | qs | qs | qs | qs | qs | qs | qs | qs |
|  | 112.38 | 124.75 | 124.75 | 124.75 | 124.75 | 112.38 | 124.75 | 124.75 | 124.75 |
| *Coating layer b)* | | | | | | | | | |
| Sodium alginate | 33.71 | — | 37.43 | 74.85 | 99.8 | 33.71 | — | 37.43 | 74.85 |
| Talc | 16.86 | — | 18.72 | 37.43 | 49.9 | 16.86 | — | 18.72 | 37.43 |
| Water | qs | — | qs | qs | qs | qs | — | qs | qs |
|  | 162.95 | — | 180.90 | 237.03 | 274.45 | 162.95 | — | 180.90 | 237.03 |

TABLE 3-continued

Examples F13-F21

| | Formulation | | | | | | | | |
|---|---|---|---|---|---|---|---|---|---|
| Ingredients/main polymer components (% SA + % L) | F13/C13 7.5% RS + 30% SA + 20% L (50%) | F14/C14 15% RS, 20% L | F15/C15 15% RS + 30% SA + 20% L (50%) | F16 15% RS + 60% SA + 20% L (80%) | F17 15% RS + 80% SA + 20% L (100%) | F18 7.5% RS + 30% SA + 40% L (70%) | F19/C19 15% RS + 40% L | F20 15% RS + 30% SA + 40% L (70%) | F21 15% RS + 60% SA + 40% L (100%) |
| Coating layer c) | | | | | | | | | |
| EUDRAGIT ® L30-D55 | 32.59* | 24.95* | 36.18* | 47.41* | 54.89* | 65.18* | 49.90* | 72.36* | 94.82* |
| TEC | 3.30 | 2.50 | 3.62 | 4.74 | 5.49 | 6.52 | 4.99 | 7.24 | 9.48 |
| Talc | 16.30 | 12.48 | 18.09 | 23.70 | 27.45 | 32.59 | 24.95 | 36.18 | 47.4 |
| Water | qs | qs | qs | qs | qs | qs | qs | qs | qs |
| Total | 215.14 | 164.68 | 238.79 | 312.88 | 362.28 | 267.24 | 204.59 | 296.92 | 388.73 |

F/C = Comparative Examples;
F = Inventive Examples;
SA = Sodium Alginate;
RS = EUDRAGIT ® RS;
L = EUDRAGIT ® L 100-55 (dry) out of EUDRAGIT ® L 30D-55;
*= Dry polymer;

Step I: Preparation of Metoprolol Succinate Pellets (16/20#) for Coating Trials
Procedure:
1) Metoprolol succinate, Avicel PH 101 and microcrystalline cellulose CL 611 were sifted through 40#sieve and mixed for 20 min in RMG at slow speed.
2) Water was added to step 1 in RMG under mixing at slow speed, total water added in 3 min. The wet mass was mixed in RMG at slow speed for 2 min with chopper started for 2 min at slow speed.
3) Wet Mass from step 2 was extruded using single screw axial extruder with counter clockwise screw rotation and 1 mm screen. Screw speed was 50 rpm and extrusion pressure was 2.1-2.6 bar.
4) Extrudates of step 3 were spheronised at 1700 to 1800 rpm for 5.0 min to get pellets.
5) Pellets were dried at 50° C. till LOD of pellets was achieved <2% at 105° C.

Step II: EUDRAGIT® RS 30D Coating Over Metoprolol Pellets
Procedure:
1. Talc and TEC was homogenized in water for 20 min
2. Talc dispersion was then added to EUDRAGIT RS30D dispersion under stirring
3. Prepared dispersion was mixed under stirring for 15 min
4. Dispersion was filtered through 60#sieve and taken for coating trial
5. Coated pellets were cured at 40° C. for 2 hours in tray dryer
6. In process and machine parameters are given in table below

TABLE 4

In-process and machine parameters

| Parameters | Observed values | Parameters | Observed values |
|---|---|---|---|
| Inlet temp. (° C.) | 30-42 | Atom. Air pressure (bar) | 1.0-1.1 |
| Product temp. (° C.) | 23-31 | Inlet RH (%) | 14-34 |
| Filter shaking (sec) | 3-5 | Exhaust RH (%) | 38-58 |
| Filter shaking pause (sec) | 150-250 | Silicon tube ID (mm) | 3 |
| Blower drive speed (%) | 52-71 | Spray rate (gm/min) | 1.5-14 |
| Air flow (cfm) | 66-96 | Base plate | B |

Step III: Sodium alginate coating between inner Eudragit RS coat and outer Eudragit FS/L coat
Cores: EUDRAGIT® RS coated Metoprolol succinate pellets
Procedure:
1. Talc was homogenized in 1/10th quantity of water for 20 min
2. Sodium alginate was dissolved in remaining water for 30 min
3. Talc dispersion was then added to sodium alginate dispersion under stirring
4. Prepared dispersion was mixed under stirring for 15 min
5. Dispersion was filtered through 60#sieve and taken for coating trial
6. In process and machine parameters are given in table below

TABLE 5

In-process and machine parameters

| Parameters | Observed values | Parameters | Observed values |
|---|---|---|---|
| Inlet temp. (° C.) | 36-80 | Atom. Air pressure (bar) | 1.2-1.5 |
| Product temp. (° C.) | 30-53 | Inlet RH (%) | 3-27 |
| Filter shaking (sec) | 3-4 | Exhaust RH (%) | 11-33 |
| Filter shaking pause (sec) | 150-240 | Silicon tube ID (mm) | 3 |

TABLE 5-continued

In-process and machine parameters

| Parameters | Observed values | Parameters | Observed values |
|---|---|---|---|
| Blower drive speed (%) | 47-81 | Spray rate (gm/min) | 1.2-18 |
| Air flow (cfm) | 66-104 | Base plate | B |

Step IV A: EUDRAGIT® FS Coating on Eudragit® RS and Sodium Alginate Coated Pellets Procedure:
1. Talc and TEC was homogenized in water for 20 min
2. Talc dispersion was then added to EUDRAGIT FS 30 D dispersion under stirring
3. Prepared dispersion was mixed under stirring for 15 min
4. Dispersion was filtered through 60#sieve and taken for coating trial
5. In process and machine parameters are mentioned in the table below

TABLE 6

In-process and machine parameters

| Parameters | |
|---|---|
| Inlet temp. (° C.) | 20-32 |
| Product temp (° C.) | 20-25 |
| Air flow (m3/h) | 24-32 |
| Atom. air pressure | 1.0-1.1 |
| Inlet RH (%) | 45-55 |
| Exhaust RH (%) | 41-83 |
| Silicon tube ID (mm) | 2 |
| Spray rate (gm/min) | 0.8-4 |
| Bowl used | Small |

Step IV B: EUDRAGIT® L Coating Over EUDRAGIT® RS and Sodium Alginate Coated Pellets Procedure:
1. Talc and TEC was homogenized in water for 20 min
2. Talc dispersion was then added to EUDRAGIT L 30 D-55 dispersion under stirring
3. Prepared dispersion was mixed under stirring for 15 min
4. Dispersion was filtered through 60#sieve and taken for coating trial
5. Pellets were transferred to Huttlin container and coating was initiated
6. In process parameters and machine parameters are mentioned in table below

TABLE 7

In-process and machine parameters

| Parameters | |
|---|---|
| Inlet temp. (° C.) | 28-41 |
| Product temp (° C.) | 27-29 |
| Air flow (m3/h) | 25-36 |
| Atom. air pressure | 1.0-1.1 |
| Inlet RH (%) | 43-66 |
| Exhaust RH (%) | 42-73 |
| Silicon tube ID (mm) | 2 |
| Spray rate (gm/min) | 0.8-3.5 |
| Bowl used | Small |

Results and Discussion of EUDRAGIT® FS Coating on EUDRAGIT® RS and Sodium Alginate Coated Pellets

TABLE NO.8

Dissolution Profiles

| Medium | Time (Hr.) | F1/C1 | F2/C2 | F3/C3 | F4/C4 | F5 | F6 | F7 | F8/C8 | F9 | F10 | F11 | F12 |
|---|---|---|---|---|---|---|---|---|---|---|---|---|---|
| | | | | | | | % Release | | | | | | |
| Acid stage pH 1.2 | 0 | 0.0 | 0.0 | 0.0 | 0.0 | 0 | 0 | 0.0 | 0.0 | 0.0 | 0.0 | 0.0 | 0.0 |
| | 2.00 | 0.0 | 0.1 | 0.0 | 0.0 | 0.00 | 0.00 | 0.0 | 0.1 | 0.0 | 0.0 | 0.0 | 0.0 |
| Buffer stage- pH 6.8 | 3.00 | 0.0 | 0.1 | 0.0 | 0.0 | 0.00 | 0.03 | 0.0 | 0.1 | 0.0 | 0.0 | 0.0 | 0.1 |
| Buffer stage- pH 7.4 | 4.00 | 3.4 | 0.2 | 0.0 | 0.5 | 0.00 | 0.39 | 0.10 | 0.1 | 0.0 | 0.0 | 0.0 | 0.1 |
| | 5.00 | 52.4 | 1.2 | 1.6 | 7.8 | 1.83 | 3.21 | 9.0 | 0.2 | 0.3 | 1.4 | 0.0 | 1.1 |
| | 6.00 | 82.5 | — | — | — | — | — | 50.1 | — | — | — | — | — |
| | 7.00 | — | 75.5 | 62.4 | 60.7 | 43.51 | 45.44 | — | 32.0 | 33.5 | 52.9 | 36.7 | 21.4 |
| | 8.00 | 95.4 | — | — | — | — | — | 85.2 | — | — | — | — | — |
| | 9.00 | — | 94.5 | 84.3 | 76.6 | 70.07 | 74.92 | — | 88.3 | 74.0 | 74.4 | 69.8 | 60.0 |
| | 10.00 | 98.4 | — | — | — | — | — | 92.9 | — | — | — | — | — |
| 40% ethanolic medium pH 1.2 | 2.00 | 13.4 | 50.80 | 23.3 | 44.3 | 2.4 | 1.2 | 4.50 | 17.7 | 3.90 | 4.8 | 0.0 | 1.6 |

Results and Discussion of EUDRAGIT® L Coating Over EUDRAGIT® RS and Sodium Alginate Coated Pellets

TABLE NO.9

Dissolution Profiles

| Medium | Time (Hr.) | F13/C13 | F14/C14 | F15/C15 | F16 | F17 | F18 | F19/C19 | F20 | F21 |
|---|---|---|---|---|---|---|---|---|---|---|
| | | | | | % Release | | | | | |
| Acid stage pH 1.2 | 0 | 0 | 0.00 | 0.0 | 0 | 0 | 0.0 | 0.0 | 0.0 | 0 |
| | 2.00 | 0.1 | 0.00 | 0.0 | 0.20 | 0.22 | 0.0 | 0.0 | 0.0 | 0.00 |
| Buffer stage - pH 6.8 | 3.00 | 5.7 | 0.31 | 0.1 | 0.83 | 0.94 | 2.5 | 0.0 | 0.1 | 0.31 |
| | 4.00 | — | 7.64 | 0.8 | 5.54 | 7.14 | 27.9 | 0.6 | 0.4 | 2.41 |

TABLE NO.9-continued

| | | | | | Dissolution Profiles | | | | | |
|---|---|---|---|---|---|---|---|---|---|---|
| Medium | Time (Hr.) | F13/C13 | F14/C14 | F15/C15 | F16 | F17 | F18 | F19/C19 | F20 | F21 |
| | | | | | % Release | | | | | |
| | 5.00 | — | 38.15 | 8.6 | 29.12 | 31.76 | 52.7 | 8.9 | 3.1 | 11.39 |
| | 6.00 | — | 71.48 | 32.3 | 54.72 | 55.92 | 66.6 | 37.6 | 15.2 | 49.53 |
| | 8.00 | — | 93.77 | 62.7 | 75.31 | 77.53 | 79.7 | 82.4 | 46.3 | 61.21 |
| | 10.00 | — | — | — | — | — | 86.4 | — | — | — |
| 40% ethanolic medium pH 1.2 | | 38.40 | 85.60 | 21.3 | 5.3 | 0.2 | 7.20 | 46.70 | 3.2 | 0.4 |

Formulations F1, F2, F3, F4, F8, F13, F14, F15 and F19 release more than 10% drug in 40% ethanolic 0.1N HCl in 2 hrs time, and hence failed to give ethanol resistance.
Formulations F5, F6, F7, F9, F10, F11, F12, L16, F17, F18, F20 and F21 release less than 10% drug in 40% ethanolic 0.1N HCl in 2 hrs time, thus provides ethanol resistance.

II. Batches with EUDRAGIT® NE (Dry Polymer) in the Coating Layer a2):

Dry polymer; F/C=Comparative Examples; F=Inventive Examples; SA=Sodium Alginate; RS=EUDRAGIT® RS; L=EUDRAGIT® L 100-55 (dry) out of EUDRAGIT® L 30D-55; S=EUDRAGIT® S 100; FS=EUDRAGIT® FS (dry) out of EUDRAGIT® FS 30D Step I: Preparation of Metoprolol Succinate Pellets (16/20#) for Coating Trials Procedure same as mentioned for Metoprolol pellets in previous section Step II. EUDRAGIT® NE Coating Over Metoprolol Pellets Procedure:

1. Talc was homogenized in one part of water for 20 min and HPC-LM was dissolved in another part.

TABLE 10

| | Formula composition | | | | | |
|---|---|---|---|---|---|---|
| | Formulation | | | | | |
| Ingredients/main polymer components (% SA + % L/S/FS) | F22/C22 5% NE + 30% SA + 20% L (50%) | F23 5% NE + 30% SA + 40% L (70%) | F24/C24 5% NE + 10% SA + 20% S (30%) | F25 5% NE + 10% SA + 40% S (50%) | F26/C26 5% NE + 10% SA + 20% FS (30%) | F27 5% NE + 10% SA + 40% FS (50%) |
| Inner core a1) of the Core a) | | | | | | |
| Metoprolol succinate | 50 | 50 | 50 | 50 | 50 | 50 |
| MCC (Avicel PH 101) | 20 | 20 | 20 | 20 | 20 | 20 |
| MCC CL 611 | 30 | 30 | 30 | 30 | 30 | 30 |
| Water | qs | qs | qs | qs | qs | qs |
| | 100.00 | 100.00 | 100.00 | 100.00 | 100.00 | 100.00 |
| Coating layer a2) of the Core a) | | | | | | |
| EUDRAGIT® NE 30 D | 5.00* | 5.00* | 5.00* | 5.00* | 5.00* | 5.00* |
| HPC-LM | 0.60 | 0.60 | 0.60 | 0.60 | 0.60 | 0.60 |
| Talc | 2.50 | 2.50 | 2.50 | 2.50 | 2.50 | 2.50 |
| Water | qs | qs | qs | qs | qs | qs |
| | 108.10 | 108.10 | 108.10 | 108.10 | 108.10 | 108.10 |
| Coating layer b) | | | | | | |
| Sodium alginate | 32.43 | 32.43 | 10.81 | 10.81 | 10.81 | 10.81 |
| Talc | 16.23 | 16.23 | 5.41 | 5.41 | 5.41 | 5.41 |
| Water | qs | qs | qs | qs | qs | qs |
| | 156.76 | 156.76 | 124.32 | 124.32 | 124.32 | 124.32 |
| Coating layer c) | | | | | | |
| EUDRAGIT® L30-D55 or EUDRAGIT® S100 or EUDRAGIT® FS 30D | 31.35* | 62.70* | 24.86 | 49.73* | 24.86* | 49.73* |
| TEC | 3.14 | 6.27 | 2.49 | 4.97 | 1.24 | 2.49 |
| Talc | 15.68 | 31.35 | 12.43 | 24.87 | 12.43 | 24.87 |
| Water | qs | qs | 5% | 5% | qs | qs |
| Acetone | — | — | 38% | 38% | — | — |
| IPA | — | — | 57% | 57% | — | — |
| Total | 188.11 | 257.08 | 164.10 | 203.89 | 162.85 | 201.41 |

2. Eudragit NM 30 D was added to HPC-LM solution under stirring
3. Talc dispersion was added to step 2 dispersion and stirring was continued for 15 minutes
4. Dispersion of step 4 was filtered through 60#sieve and taken for coating trial
5. Coated pellets were cured at 50° C. for 24 hours in tray dryer
6. In process and machine parameters are given in table below

TABLE 11

In-process and machine parameters

| Parameters | Observed values | Parameters | Observed values |
|---|---|---|---|
| Inlet temp. (° C.) | 29-34 | Atom. Air pressure (bar) | 1.0-1.1 |
| Product temp. (° C.) | 26-27 | Inlet RH (%) | 20-24 |
| Filter shaking (sec) | 4 | Exhaust RH (%) | 34-40 |
| Filter shaking pause (sec) | 250 | Silicon tube ID (mm) | 3 |
| Blower drive speed (%) | 55-66 | Spray rate (gm/min) | 2.1-7 |
| Air flow (cfm) | 70-76 | Base plate | B |

Step III. Sodium Alginate Coating Over 5% EUDRAGIT® NE Coated Metoprolol Pellets Formula composition and procedure for Sodium alginate dispersion preparation same as mentioned in the previous section

TABLE 12

In-process and machine parameters

| Parameters | Observed values | Parameters | Observed values |
|---|---|---|---|
| Inlet temp. (° C.) | 32-74 | Atom. Air pressure (bar) | 1.2-1.4 |
| Product temp. (° C.) | 28-53 | Inlet RH (%) | 3-27 |
| Filter shaking (sec) | 4 | Exhaust RH (%) | 11-33 |
| Filter shaking pause (sec) | 250 | Silicon tube ID (mm) | 3 |
| Blower drive speed (%) | 65-76 | Spray rate (gm/min) | 1.5-17 |
| Air flow (cfm) | 73-76 | Base plate | B |

Step III a: EUDRAGIT® L Coating on EUDRAGIT® NE and Sodium Alginate Coated Pellets Formula composition and procedure for Eudragit L dispersion preparation same as mentioned in the previous section

TABLE 13

In-process and machine parameters

| Parameters | Observed values | Parameters | Observed values |
|---|---|---|---|
| Inlet temp. (° C.) | 28-38 | Exhaust RH (%) | 36-64 |
| Product temp (° C.) | 26-28 | Silicon tube ID (mm) | 2 |
| Air flow (m3/h) | 25-32 | Spray rate (gm/min) | 0.8-3.2 |
| Atom. air pressure | 1.0 | Bowl used | Small |
| Inlet RH (%) | 38-62 | | |

Step III b: EUDRAGIT® FS Coating on EUDRAGIT® NE and Sodium Alginate Coated Pellets Procedure for Eudragit FS dispersion preparation same as mentioned in the previous section

TABLE 14

In-process and machine parameters

| Parameters | Observed values | Parameters | Observed values |
|---|---|---|---|
| Inlet temp. (° C.) | 25-32 | Exhaust RH (%) | 39-74 |
| Product temp (° C.) | 21-24 | Silicon tube ID (mm) | 2 |
| Air flow (m3/h) | 25-35 | Spray rate (gm/min) | 0.5-3.2 |
| Atom. air pressure | 1.0-1.1 | Bowl used | Small |
| Inlet RH (%) | 44-58 | | |

Step IIIc: EUDRAGIT® S Coating on EUDRAGIT® NE and Sodium Alginate Coated Pellets Formula composition and procedure for Eudragit S dispersion preparation same as mentioned in the previous section

TABLE 15

In-process and machine parameters

| Parameters | Observed values | Parameters | Observed values |
|---|---|---|---|
| Inlet temp. (° C.) | 28-37 | Exhaust RH (%) | 29-46 |
| Product temp (° C.) | 24-30 | Silicon tube ID (mm) | 2 |
| Air flow (m3/h) | 25-33 | Spray rate (gm/min) | 0.5-3.2 |
| Atom. air pressure | 1.0-1.1 | Bowl used | Small |
| Inlet RH (%) | 25-56 | | |

Results and Discussion:

TABLE 16

Dissolution Profiles

| Medium | Time (Hr.) | F22/C22 | F23 | F24/C24 | F25 | Medium | Time (Hr.) | F26/C26 | F27 |
|---|---|---|---|---|---|---|---|---|---|
| | | % Release | | | | | | % Release | |
| Acid stage | 0 | 0.0 | 0.0 | 0.0 | 0.0 | Acid stage | 0 | 0.0 | 0.0 |
| pH 1.2 | 2.00 | 0.0 | 0.0 | 0.1 | 0.0 | | 2.00 | 0.0 | 0.0 |
| Buffer stage-6.8 | 3.00 | 2.6 | 2.8 | 3.0 | 0.3 | Buffer stage-6.8 | 3.00 | 0.1 | 0.1 |
| | 4.00 | 13.6 | 14.7 | 14.6 | 2.6 | Buffer stage-7.4 | 4.00 | 2.7 | 0.2 |
| | 5.00 | 30.4 | 31.4 | 33.8 | 11.5 | | 5.00 | 18.6 | 7.2 |
| | 6.00 | 46.5 | 47.5 | 51.4 | 26.5 | | 6.00 | 42.1 | 29.0 |
| | 8.00 | 72.1 | 70.3 | 74.6 | 55.7 | | 8.00 | 76.9 | 70.4 |
| | 10.00 | 86.3 | 83.1 | 84.7 | 73.8 | | 10.00 | 92.4 | 87.8 |
| | 12.00 | 93.7 | 89.5 | 91.3 | 82.8 | | 12.00 | 97.6 | 95.9 |

TABLE 16-continued

| Medium | Time (Hr.) | F22/C22 | F23 | F24/C24 | F25 | Medium | Time (Hr.) | F26/C26 | F27 |
|---|---|---|---|---|---|---|---|---|---|
| | | | % Release | | | | | % Release | |
| 40% ethanolic medium pH 1.2 | 2 hrs | 16.8 | 7.3 | 25.1 | 2.3 | | | 16.6 | 2.7 |

Formulations F22, F24 and F26 release more than 10% drug in 40% alcoholic 0.1N HCl in 2 hr time, thus failed to give ethanol resistance.
Formulations F23, F25 and F27 release less than 10% drug in 40% alcoholic 0.1N HCl in 2 hrs time, thus provides ethanol resistance III. Batches with Ethyl Cellulose in the Coating Layer a2):

TABLE 17

Examples F28-F29, Formula composition

| Formulation | F28 | F29 |
|---|---|---|
| Ingredients/Main Poymer components (% SA + % L/FS) | 10% EC + 30% SA + 40% L (70%) | 10% EC + 10% SA + 40% FS (50%) |
| Metoprolol succinate | 50 | 50 |
| MCC (Avicel PH 101) | 20 | 20 |
| MCC CL 611 | 30 | 30 |
| Water | qs | qs |
| | 100.00 | 100.00 |
| Ethyl cellulose | 10.00 | 10.00 |
| HPC-LM | 4.00 | 4.00 |
| Dibutyl sebacate | 0.25 | 0.25 |
| IPA (70%) | qs | qs |
| Acetone (30%) | qs | qs |
| | 114.25 | 114.25 |
| Sodium alginate | 34.28 | 11.43 |
| Talc | 17.14 | 5.76 |
| Water | qs | qs |
| | 165.67 | 131.44 |
| EUDRAGIT® L30-D55 | 66.27* | — |
| EUDRAGIT® FS 30 D | — | 52.58* |
| TEC | 6.63 | 2.63 |
| Talc | 33.14 | 26.29 |
| Water | qs | qs |
| Total | 271.71 | 212.94 |

*Dry polymer; F = Inventive Examples; SA = Sodium Alginate; EC = Ethyl Cellulose; L = EUDRAGIT® L 100-55 (dry) out of EUDRAGIT® L 30D-55; FS = EUDRAGIT® FS (dry) out of EUDRAGIT® FS 30D Step I: Preparation of Metoprolol Succinate Pellets (16/20#) for Coating Trials Procedure same as mentioned for Metoprolol pellets in previous section Step II. Ethyl Cellulose Coating Over Metoprolol Pellets Procedure:

1. IPA: Acetone (70:30) were taken and dibutyl sebacate was added to under stirring
2. HPC-LM followed by ethyl cellulose was dissolved in step 1 solution under stirring
3. Solution of step 2 was taken for coating trial
4. In process drying was done at 50° C. for 30 minutes
5. In process and machine parameters are given in table below

TABLE 18

In-process and machine parameters

| Parameters | Observed values | Parameters | Observed values |
|---|---|---|---|
| Inlet temp. (° C.) | 25-31 | Atom. Air pressure (bar) | 1.1 |
| Product temp. (° C.) | 23-25 | Inlet RH (%) | 28-39 |
| Filter shaking (sec) | 4 | Exhaust RH (%) | 35-41 |
| Filter shaking pause (sec) | 250 | Silicon tube ID (mm) | 3 |
| Blower drive speed (%) | 60-75 | Spray rate (gm/min) | 2-10 |
| Air flow (cfm) | 88-105 | Base plate | B |

Step III. Sodium Alginate Coating Over 10% Ethyl Cellulose Coated Metoprolol Pellets Formula composition and procedure for Sodium alginate dispersion preparation same as mentioned in the previous section

TABLE 19

In-process and machine parameters

| Parameters | Observed values | Parameters | Observed values |
|---|---|---|---|
| Inlet temp. (° C.) | 43-78 | Atom. Air pressure (bar) | 1.2-1.4 |
| Product temp. (° C.) | 36-54 | Inlet RH (%) | 3-10 |
| Filter shaking (sec) | 4 | Exhaust RH (%) | 13-24 |
| Filter shaking pause (sec) | 240 | Silicon tube ID (mm) | 3 |
| Blower drive speed (%) | 65-82 | Spray rate (gm/min) | 2-16 |
| Air flow (cfm) | 80-109 | Base plate | B |

Step III a: EUDRAGIT® L Coating on Ethyl Cellulose and Sodium Alginate Coated Pellets Formula composition and procedure for EUDRAGIT® L dispersion preparation same as in the previous section

TABLE 20

In-process and machine parameters

| Parameters | Observed values | Parameters | Observed values |
|---|---|---|---|
| Inlet temp. (° C.) | 28-38 | Exhaust RH (%) | 53-58 |
| Product temp (° C.) | 23-27 | Silicon tube ID (mm) | 2 |
| Air flow (m3/h) | 20-25 | Spray rate (gm/min) | 0.8-3.2 |
| Atom. air pressure | 1.0 | Bowl used | Small |
| Inlet RH (%) | 44-73 | | |

Step III b: EUDRAGIT® FS Coating on Ethyl Cellulose and Sodium Alginate Coated Pellets Procedure for EUDRAGIT®FS dispersion preparation same as mentioned in the previous section

TABLE 21

In-process and machine parameters

| Parameters | Observed values | Parameters | Observed values |
|---|---|---|---|
| Inlet temp. (° C.) | 22-30 | Exhaust RH (%) | 52-66 |
| Product temp (° C.) | 25-27 | Silicon tube ID (mm) | 2 |
| Air flow (m3/h) | 25 | Spray rate (gm/min) | 0.8-2.8 |
| Atom. air pressure | 1.0 | Bowl used | Small |
| Inlet RH (%) | 46-59 | | |

Results and Discussion:

TABLE 22

Examples F28 and F29, Dissolution Profile
Formulations F28 and F29 releases less than 10% drug in 40% alcoholic 0.1N HCl in 2 hr time, thus provides alcohol resistance

| Medium | Time (Hr.) | F28 % Release | Medium | Time (Hr.) | F29 % Release |
|---|---|---|---|---|---|
| Acid stage | 0 | 0.0 | Acid stage | 0 | 0.0 |
|  | 2.00 | 0.0 |  | 2.00 | 0.0 |
| Buffer stage-6.8 | 3.00 | 0.3 | Buffer stage-6.8 | 3.00 | 0.0 |
|  | 4.00 | 7.9 | Buffer stage-7.4 | 4.00 | 0.1 |
|  | 5.00 | 32.7 |  | 5.00 | 6.0 |
|  | 6.00 | 54.1 |  | 6.00 | 36.1 |
|  | 8.00 | 74.6 |  | 8.00 | 73.2 |
|  | 10.00 | 82.7 |  | 10.00 | 85.9 |
|  | 12.00 | 87.0 |  | 12.00 | 92.4 |
| 40% Alcoholic media | 2 hrs | 0.20 |  | 2 hrs | 0.80 |

Example Formulation with Acetaminophen as Model Drug:

TABLE NO: 23

Examples F30-F32, Formula Composition

| Formulation | F30 | F31 | F32 |
|---|---|---|---|
| Ingredients/main polymer components (% SA + % L/FS) | 15% RS + 30% SA + 40% L (70%) | 15% RS + 10% SA + 40% FS (50%) | 15% RS + 30% SA + 20% FS (50%) |
| Acetaminophen | 50 | 50 | 50 |
| MCC(Avicel PH 101) | 20 | 20 | 20 |
| Vivapur MCG 611 | 30 | 30 | 30 |
| Water | qs | qs | qs |
|  | 100.00 | 100.00 | 100.00 |
| EUDRAGIT ® RS 30D | 15.00* | 15.00* | 15.00* |
| TEC | 2.25 | 2.25 | 2.25 |
| Talc | 7.50 | 7.50 | 7.50 |
| Water | qs | qs | qs |
|  | 124.75 | 124.75 | 124.75 |
| Sodium alginate (Protanal CR) | 37.43 | 12.48 | 37.43 |
| Talc | 18.72 | 6.24 | 18.72 |
| Water | qs | qs | qs |
|  | 180.90 | 143.75 | 180.90 |
| EUDRAGIT ® L30D 55 | 72.36* | — | — |
| EUDRAGIT ® FS30D | — | 57.50* | 36.18* |
| TEC | 7.24 | 2.88 | 1.81 |
| Talc | 36.18 | 28.75 | 18.09 |
| Water | qs | qs | qs |
| Total | 296.92 | 232.88 | 236.98 |

*Dry polymer; F/C = Comparative Examples; F = Inventive Examples; SA = Sodium Alginate; RS = EUDRAGIT ® RS; L = EUDRAGIT ® L 100-55 (dry) out of EUDRAGIT ® L 30D-55; FS = EUDRAGIT ® FS (dry) out of EUDRAGIT ® FS 30D Step I: Preparation of Acetaminophen Pellets (16/20#) for Coating Trials Procedure and Process Parameters:

Same as for Metoprolol pellets mentioned in previous section

Step II. EUDRAGIT® RS Coating Over Acetaminophen Pellets (#16/20):

Formula composition and procedure for Eudragit® RS dispersion same as mentioned in previous sections of Metoprolol

TABLE 24

In-process and machine parameters

| Parameters | Observed values | Parameters | Observed values |
|---|---|---|---|
| Inlet temp. (° C.) | 30-45 | Atom. Air pressure (bar) | 1.1-1.2 |
| Product temp. (° C.) | 28-29 | Inlet RH (%) | 14-35 |
| Filter shaking (sec) | 4 | Exhaust RH (%) | 29-44 |
| Filter shaking pause (sec) | 250 | Silicon tube ID (mm) | 3 |
| Blower drive speed (%) | 65-70 | Spray rate (gm/min) | 2.1-15 |
| Air flow (cfm) | 85-87 | Base plate | B |

Step III. 10% and 30% Sodium Alginate Coating on 15% EUDRAGIT® RS Coated Acetaminophen Pellets Formula composition and procedure for Sodium alginate dispersion same as mentioned in previous sections of Metoprolol

TABLE 25

In-process and machine parameters

| Parameters | Observed values | Parameters | Observed values |
|---|---|---|---|
| Inlet temp. (° C.) | 40-77 | Atom. Air pressure (bar) | 1.2-1.4 |
| Product temp. (° C.) | 32-53 | Inlet RH (%) | 3-13 |
| Filter shaking (sec) | 4 | Exhaust RH (%) | 9-29 |
| Filter shaking pause (sec) | 250 | Silicon tube ID (mm) | 3 |
| Blower drive speed (%) | 68-90 | Spray rate (gm/min) | 1.2-13 |
| Air flow (cfm) | 72-96 | Base plate | B |

Step III a: EUDRAGIT® L Coating on EUDRAGIT® RS and Sodium Alginate Coated Pellets Formula and procedure for Eudragit L dispersion preparation same as mentioned in previous section

TABLE 26

In-process and machine parameters

| Parameters | Observed values | Parameters | Observed values |
|---|---|---|---|
| Inlet temp. (° C.) | 28-38 | Exhaust RH (%) | 54-58 |
| Product temp (° C.) | 26-29 | Silicon tube ID (mm) | 2 |
| Air flow (m3/h) | 25-30 | Spray rate (gm/min) | 0.8-3.2 |
| Atom. air pressure | 1.0 | Bowl used | Small |
| Inlet RH (%) | 54-68 | | |

Step III b: EUDRAGIT® FS Coating on EUDRAGIT® RS and Sodium Alginate Coated Pellets Formula composition and procedure for EUDRAGIT® FS dispersion preparation same as mentioned in previous section

TABLE 27

In-process and machine parameters

| Parameters | Observed values | Parameters | Observed values | Parameters |
|---|---|---|---|---|
| Inlet temp. (° C.) | 20-32 | 20-30 | Exhaust RH (%) | 51-56 |
| Product temp (° C.) | 20-23 | 20-23 | Silicon tube ID (mm) | 2 |
| Air flow (m3/h) | 25-30 | 25-30 | Spray rate (gm/min) | 0.8-3.2 |
| Atom. air pressure | 1.0-1.1 | 1.0-1.1 | Bowl used | Small |
| Inlet RH (%) | 57-77 | 54-81 | | |

Results and Discussion:

TABLE 28

Dissolution Profile

| Medium | Time (Hr.) | F30 % Release | Medium | Time (Hr.) | F31 % Release | F32 % Release |
|---|---|---|---|---|---|---|
| Acid stage | 0 | 0.00 | Acid stage | 0 | 0.00 | 0.00 |
| pH 1.2 | 2.00 | 0.00 | pH 1.2 | 2.00 | 0.00 | 0.00 |
| Buffer stage-6.8 | 3.00 | 0.40 | Buffer stage-pH 6.8 | 3.00 | 0.00 | 0.00 |
| | 4.00 | 1.50 | Buffer stage-pH 7.4 | 4.00 | 0.00 | 0.80 |
| | 5.00 | 3.40 | | 5.00 | 0.50 | 4.60 |
| | 6.00 | 6.00 | | 6.00 | 2.00 | 10.80 |
| | 8.00 | 12.70 | | 8.00 | 9.50 | 26.80 |
| | 10.00 | 21.00 | | 10.00 | 22.50 | 44.90 |
| | 12.00 | 30.20 | | 12.00 | 36.30 | 61.10 |
| 40% ethanolic medium pH 1.2 | 2 hrs | 0.60 | | | 0.00 | 0.00 |

Formulations F30, F31 and F32 releases less than 10% drug in 40% alcoholic 0.1N HCl in 2 hr time, thus provides alcohol resistance.

The invention claimed is:

1. A pharmaceutical or nutraceutical composition, comprising:
 a core a) comprising an active ingredient and a water-insoluble polymer which is a (meth)acrylate copolymer;
 a coating layer b) above the core a) comprising a salt of an alginic acid; and
 a coating layer c) above the coating layer b) comprising an anionic (meth)acrylate copolymer polymerized from a (meth)acrylate monomer mixture comprising 5-75% by weight, in relation to a total weight of the (meth)acrylate monomer mixture, of (meth)acrylate monomers with an anionic group,
 wherein:
 an amount of the water-insoluble polymer in the core a) is 2 to 50% by weight in relation to a weight of the core a);
 an amount of the salt of an alginic acid in the coating layer b) is 5 to 85% by weight in relation to the weight of the core a); and
 an amount of the anionic (meth)acrylate copolymer in the coating layer c) is 10 to 75% by weight in relation to the weight of the core a) and the coating layer b); and
 when the amount of polymerized monomers with anionic groups of the anionic (meth)acrylate copolymer comprised in the coating layer c) is 5 to 40% by weight in relation to a total weight of the polymerized monomers, percentages of the amount of the salt of the alginic acid in the coating layer b) in relation to the weight of the core a) and percentages of the amount of the anionic (meth) acrylate copolymer in the coating layer c) in relation to the weight of the core a) and the coating layer b) add up to at least 50%, and when the amount of polymerized monomers with anionic groups of the anionic (meth)acrylate copolymer comprised in the coating layer c) is more than 40 and up to 75% by weight in relation to the total weight of the polymerized monomers,
the percentages of the amount of the salt of the alginic acid in the coating layer b) in relation to the weight of the core a) and the percentages of the amount of the anionic (meth)acrylate copolymer in the coating layer c) in relation to the weight of the core a) and the coating layer b) add up to at least 60%; and
wherein release of the pharmaceutical or nutraceutical active ingredient is less than 60% after 4 hours and at least 60% after 6 to 10 hours under in-vitro conditions at pH 1.2 for 2 hours and subsequent buffered medium at pH 6.8 or at pH 7.4 according to USP32 for a remaining time.

2. The pharmaceutical or nutraceutical composition according to claim 1, wherein:
 the core a) comprises an inner core a1), comprising the active ingredient and a coating layer a2), comprising the water-insoluble polymer; and
 the coating layer a2) is above the inner core a1) and below the coating layer b).

3. The pharmaceutical or nutraceutical composition according to claim 1, wherein the water-insoluble polymer is a (meth)acrylate copolymer polymerized from a monomer mixture comprising 88 to 98% by weight of at least one $C_1$ to $C_4$ alkyl ester of (meth)acrylic acid and 2 to 12% by weight of at least one alkyl(meth)acrylate monomer with a quaternary ammonium group in the alkyl radical.

4. The pharmaceutical or nutraceutical composition according to claim 1, wherein the water-insoluble polymer is a (meth)acrylate copolymer which is polymerized from a monomer mixture comprising more than 95 and up to 100% by weight of at least one $C_1$ to $C_4$ alkyl ester of (meth)acrylic acid and 0 to less than 5% by weight of at least one (meth)acrylate monomer with an anionic group.

5. The pharmaceutical or nutraceutical composition according to claim 1, wherein the salt of the alginic acid used for the coating layer b) has a viscosity of 30 to 720 cP in a 1% aqueous solution (weight/weight).

6. The pharmaceutical or nutraceutical composition according to claim 1, wherein the salt of alginic acid is selected from the group consisting of sodium alginate, potassium alginate, magnesium alginate, lithium alginate, ammonium alginate, and any mixtures thereof.

7. The pharmaceutical or nutraceutical composition according to claim 1, wherein not more than 10% of the active ingredient is released under in-vitro conditions at pH 1.2 over a period of 2 hours in a medium according to USP32 with and without an addition of 40% (v/v) ethanol.

8. The pharmaceutical or nutraceutical composition according to claim 1, wherein the core a), the coating layer b), the coating layer c), or a combination thereof, comprise up to 80% by weight of at least one pharmaceutical or nutraceutically acceptable excipient.

9. A process for producing the pharmaceutical or nutraceutical composition according to claim 1, the process comprising:
   forming the core a) comprising the active ingredient by direct compression, compression of dry, wet or sintered granules, by extrusion and subsequent rounding off, by wet or dry granulation, direct pelleting or by binding powders onto active ingredient-free beads or neutral cores or active ingredient-containing particles; and
   applying the inner coating layer b) and the outer coating layer c) in the form of aqueous dispersions or organic solutions in spray processes or by fluidized bed spray granulation.

10. A sustained release gastric resistant pharmaceutical or nutraceutical composition having resistance against the influence of alcohol, comprising the pharmaceutical or nutraceutical composition of claim 1.

* * * * *